(12) United States Patent
Lockwood et al.

(10) Patent No.: US 7,896,864 B2
(45) Date of Patent: *Mar. 1, 2011

(54) VENTED VACUUM BANDAGE WITH IRRIGATION FOR WOUND HEALING AND METHOD

(76) Inventors: Jeffrey S. Lockwood, Batesville, IN (US); Robert Petrosenko, Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/684,989

(22) Filed: Mar. 12, 2007

(65) Prior Publication Data

US 2007/0156104 A1 Jul. 5, 2007

Related U.S. Application Data

(63) Continuation of application No. 10/496,623, filed as application No. PCT/US02/41228 on Dec. 20, 2002, now Pat. No. 7,195,624.

(60) Provisional application No. 60/344,588, filed on Dec. 26, 2001, provisional application No. 60/394,809, filed on Jul. 10, 2002, provisional application No. 60/394,970, filed on Jul. 10, 2002.

(51) Int. Cl.
*A61M 27/00* (2006.01)

(52) U.S. Cl. ............................. 604/541; 604/30; 604/305

(58) Field of Classification Search .................... 604/35, 604/305, 30, 45, 541, 543
See application file for complete search history.

(56) References Cited

U.S. PATENT DOCUMENTS

| 774,529 A | 11/1904 | Nieschang |
| 1,000,001 A | 8/1911 | Holz |
| 1,355,846 A | 10/1920 | Rannells |
| 1,385,346 A | 7/1921 | Taylor |
| 1,709,520 A | 4/1929 | Chandler |
| 1,936,129 A | 11/1933 | Fisk |
| 2,078,180 A | 4/1937 | Kronenberg |
| 2,195,771 A | 4/1940 | Estler |
| 2,221,758 A | 11/1940 | Elmquist |
| 2,305,289 A | 12/1942 | Coburg .......................... 128/132 |
| 2,338,339 A | 1/1944 | Lamere |
| 2,443,481 A | 6/1948 | Sene |
| 2,547,758 A | 4/1951 | Keeling ......................... 128/349 |
| 2,560,915 A * | 7/1951 | Bamberger ...................... 604/45 |
| 2,573,791 A | 11/1951 | Howells |
| 2,577,945 A | 12/1951 | Atherton |
| 2,632,443 A | 3/1953 | Lesher |
| 2,682,873 A | 7/1954 | Evens |
| 2,910,763 A | 11/1959 | Lauterbach .................. 128/72.2 |
| 2,969,057 A | 1/1961 | Simmons .......................... 128/2 |

(Continued)

FOREIGN PATENT DOCUMENTS

AU 550575 A1 8/1982

(Continued)

OTHER PUBLICATIONS

Wooding-Scott, Margaret, et al., No wound is too big for resourceful nurses, Dec. 1988, RN, pp. 22-25.*

(Continued)

*Primary Examiner* — Tatyana Zalukaeva
*Assistant Examiner* — Paula L Craig

(57) ABSTRACT

A vacuum and irrigation wound bandage system is provided for use with a wound. The system includes a vacuum source, an irrigation source, and a bandage positioned adjacent the wound to create a sealed environment around the wound. The vacuum source of the system is in communication with the bandage to create negative pressure between the bandage and the wound.

15 Claims, 12 Drawing Sheets

U.S. PATENT DOCUMENTS

| | | | |
|---|---|---|---|
| 3,026,874 A | 3/1962 | Stevens | |
| 3,066,672 A | 12/1962 | Crosby, Jr. et al. | 128/276 |
| 3,315,665 A | 4/1967 | Macleod | |
| 3,367,332 A | 2/1968 | Groves | |
| 3,382,867 A | 5/1968 | Reaves | |
| 3,430,631 A * | 3/1969 | Abramson | 604/541 |
| 3,492,991 A | 2/1970 | Dyer | |
| 3,520,300 A | 7/1970 | Flower | |
| 3,528,416 A | 9/1970 | Chamberlain | |
| 3,568,675 A | 3/1971 | Harvey | |
| 3,585,742 A | 6/1971 | Tyler | |
| 3,599,639 A | 8/1971 | Spotz | |
| 3,610,238 A | 10/1971 | Rich | |
| 3,623,087 A | 11/1971 | Gallichotte | 340/412 |
| 3,626,087 A | 12/1971 | Tomioka | 178/5.4 |
| 3,648,692 A | 3/1972 | Wheeler | |
| 3,682,180 A | 8/1972 | McFarlane | 128/350 |
| 3,683,894 A | 8/1972 | Villari | |
| 3,721,244 A | 3/1973 | Elmaleh | |
| 3,752,158 A | 8/1973 | Kariher | |
| 3,753,439 A * | 8/1973 | Brugarolas et al. | 604/43 |
| 3,782,377 A | 1/1974 | Rychlik | |
| 3,812,972 A | 5/1974 | Rosenblum | |
| 3,814,095 A | 6/1974 | Lubens | |
| 3,817,145 A | 6/1974 | Cohen | 84/471 |
| 3,823,720 A * | 7/1974 | Tribble | 604/43 |
| 3,826,254 A | 7/1974 | Mellor | 128/133 |
| 3,831,588 A | 8/1974 | Rindner | |
| 3,860,008 A | 1/1975 | Miner et al. | 604/93.01 |
| 3,874,387 A | 4/1975 | Barbieri et al. | |
| 3,903,882 A | 9/1975 | Augurt et al. | |
| 3,924,624 A | 12/1975 | Schachet | 128/276 |
| 3,935,863 A | 2/1976 | Kliger | |
| 3,954,105 A | 5/1976 | Nordby et al. | |
| 3,982,546 A | 9/1976 | Friend | |
| 4,004,590 A | 1/1977 | Muriot | |
| 4,013,076 A | 3/1977 | Puderbaugh et al. | |
| RE29,319 E | 7/1977 | Nordby et al. | |
| RE29,321 E | 7/1977 | Holbrook | |
| 4,058,123 A * | 11/1977 | May | 604/30 |
| 4,080,970 A | 3/1978 | Miller | |
| 4,096,853 A | 6/1978 | Weigand | 128/2 |
| 4,112,947 A | 9/1978 | Nehring | |
| 4,139,004 A | 2/1979 | Gonzalez | |
| 4,149,541 A | 4/1979 | Gammons et al. | |
| 4,165,748 A | 8/1979 | Johnson | 128/348 |
| 4,178,974 A | 12/1979 | Levin | |
| 4,184,510 A | 1/1980 | Murry et al. | 137/565 |
| 4,191,204 A | 3/1980 | Nehring | |
| 4,219,021 A * | 8/1980 | Fink | 137/556.6 |
| 4,224,941 A | 9/1980 | Stivala | |
| 4,233,969 A | 11/1980 | Lock et al. | 128/156 |
| 4,245,630 A | 1/1981 | Lloyd et al. | 128/155 |
| 4,250,882 A | 2/1981 | Adair | |
| 4,256,109 A | 3/1981 | Nichols | 128/276 |
| 4,261,363 A | 4/1981 | Russo | 128/350 |
| 4,275,721 A | 6/1981 | Olson | |
| 4,284,079 A | 8/1981 | Adair | 128/295 |
| 4,297,995 A | 11/1981 | Golub | |
| 4,333,468 A | 6/1982 | Geist | 128/348 |
| 4,341,209 A | 7/1982 | Schaar | |
| 4,364,394 A * | 12/1982 | Wilkinson | 604/102.02 |
| 4,373,519 A | 2/1983 | Errede et al. | |
| 4,382,441 A * | 5/1983 | Svedman | 604/291 |
| 4,392,853 A | 7/1983 | Muto | 604/171 |
| 4,392,858 A | 7/1983 | George et al. | 604/187 |
| 4,399,816 A | 8/1983 | Spangler | |
| 4,419,097 A | 12/1983 | Rowland | 604/174 |
| 4,445,897 A * | 5/1984 | Ekbladh et al. | 604/541 |
| 4,457,755 A | 7/1984 | Wilson | |
| 4,460,370 A | 7/1984 | Allison et al. | |
| 4,465,062 A | 8/1984 | Versaggi | |
| 4,465,485 A | 8/1984 | Kashmer et al. | 604/320 |
| 4,469,092 A | 9/1984 | Marshall | |
| 4,475,909 A | 10/1984 | Eisenberg | 604/349 |
| 4,480,638 A | 11/1984 | Schmid | 128/155 |
| 4,508,533 A * | 4/1985 | Abramson | 604/35 |
| 4,525,156 A * | 6/1985 | Benusa et al. | 604/28 |
| 4,525,166 A | 6/1985 | Leclerc | |
| 4,525,374 A | 6/1985 | Vaillancourt | 427/2 |
| 4,533,352 A | 8/1985 | Van Beek | |
| 4,533,419 A | 8/1985 | Pieslak | |
| 4,540,412 A | 9/1985 | Van Overloop | |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson | |
| 4,569,348 A | 2/1986 | Hasslinger | 604/179 |
| 4,569,674 A | 2/1986 | Phillips et al. | |
| 4,573,965 A * | 3/1986 | Russo | 604/30 |
| 4,579,555 A | 4/1986 | Russo | |
| 4,596,564 A * | 6/1986 | Spetzler et al. | 604/541 |
| 4,605,399 A | 8/1986 | Weston | |
| 4,608,041 A | 8/1986 | Nielsen | |
| 4,614,794 A | 9/1986 | Easton et al. | 530/356 |
| 4,624,656 A | 11/1986 | Clark | |
| 4,633,863 A | 1/1987 | Filips | |
| 4,637,819 A | 1/1987 | Ouellette et al. | |
| 4,640,688 A | 2/1987 | Hauser | 604/352 |
| 4,641,643 A | 2/1987 | Greer | |
| 4,645,492 A | 2/1987 | Weeks | |
| 4,655,210 A | 4/1987 | Edenbaum | |
| 4,655,754 A | 4/1987 | Richmond et al. | |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Fryslie | |
| 4,679,590 A | 7/1987 | Hergenroeder | |
| 4,704,102 A * | 11/1987 | Guthery | 604/28 |
| 4,710,165 A * | 12/1987 | McNeil et al. | 604/67 |
| 4,713,051 A * | 12/1987 | Steppe et al. | 604/30 |
| 4,717,332 A | 1/1988 | Edens | 431/8 |
| 4,717,379 A * | 1/1988 | Ekholmer | 604/43 |
| 4,717,382 A | 1/1988 | Clemens | |
| 4,733,659 A | 3/1988 | Edenbaum | |
| 4,735,606 A * | 4/1988 | Davison | 604/28 |
| 4,735,610 A | 4/1988 | Akkas et al. | |
| 4,737,148 A * | 4/1988 | Blake | 604/126 |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | 604/20 |
| 4,798,578 A | 1/1989 | Ranford | |
| 4,820,265 A | 4/1989 | DeSatnick et al. | |
| 4,820,284 A | 4/1989 | Hauri | |
| 4,826,494 A | 5/1989 | Richmond et al. | 604/323 |
| 4,826,949 A | 5/1989 | Stanko | 528/272 |
| 4,834,110 A | 5/1989 | Richard | |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A * | 7/1989 | Jackson | 128/207.16 |
| 4,863,449 A | 9/1989 | Therriault et al. | 604/352 |
| 4,872,450 A | 10/1989 | Austad | |
| 4,878,901 A | 11/1989 | Sachse | 604/174 |
| 4,890,608 A | 1/1990 | Steer | |
| 4,897,081 A | 1/1990 | Poirier et al. | |
| 4,900,302 A | 2/1990 | Newton | 604/30 |
| 4,902,508 A | 2/1990 | Badylak et al. | 424/95 |
| 4,906,233 A | 3/1990 | Moriuchi et al. | 604/174 |
| 4,906,240 A | 3/1990 | Reed | |
| 4,915,694 A | 4/1990 | Yamamoto et al. | |
| 4,917,112 A | 4/1990 | Kalt | |
| 4,919,654 A | 4/1990 | Kalt | 604/180 |
| 4,921,492 A | 5/1990 | Schultz et al. | |
| 4,930,997 A | 6/1990 | Bennett | |
| 4,941,882 A | 7/1990 | Ward | |
| 4,950,230 A * | 8/1990 | Kendell | 604/28 |
| 4,953,565 A | 9/1990 | Tachibana | |
| 4,956,178 A | 9/1990 | Badylak et al. | 424/551 |
| 4,957,492 A | 9/1990 | McVay | |
| 4,962,761 A | 10/1990 | Golden | |

| Patent No. | Date | Inventor | Class |
|---|---|---|---|
| 4,969,880 A * | 11/1990 | Zamierowski | 604/305 |
| 4,969,881 A | 11/1990 | Viesturs | |
| 4,970,298 A | 11/1990 | Silver et al. | 530/356 |
| 4,985,019 A | 1/1991 | Michelson | 604/180 |
| 4,988,336 A | 1/1991 | Kohn | |
| 4,990,144 A | 2/1991 | Blott | |
| 4,991,574 A | 2/1991 | Pocknell | |
| 4,994,022 A | 2/1991 | Steffler | |
| 4,997,425 A | 3/1991 | Shioya et al. | |
| 5,000,172 A | 3/1991 | Ward | |
| 5,000,741 A | 3/1991 | Kalt | |
| 5,002,528 A | 3/1991 | Palestrant | |
| 5,002,529 A | 3/1991 | Cunningham | |
| 5,003,971 A | 4/1991 | Buckley | |
| 5,014,389 A | 5/1991 | Ogilvie | |
| 5,034,003 A | 7/1991 | Denance | |
| 5,034,006 A | 7/1991 | Hosoda et al. | |
| 5,035,865 A | 7/1991 | Inaba | |
| 5,037,397 A | 8/1991 | Kalt et al. | 604/174 |
| 5,042,978 A | 8/1991 | Quenin et al. | |
| 5,045,777 A | 9/1991 | Itagaki | |
| 5,060,662 A | 10/1991 | Farnswoth | |
| 5,071,409 A | 12/1991 | Rosenberg | |
| 5,073,172 A | 12/1991 | Fell | |
| 5,080,650 A | 1/1992 | Hirsch et al. | 604/104 |
| 5,086,170 A | 2/1992 | Luheshi et al. | 540/303 |
| 5,086,763 A | 2/1992 | Hathman | |
| 5,086,764 A | 2/1992 | Gilman | |
| 5,092,858 A | 3/1992 | Benson et al. | 604/319 |
| 5,100,395 A * | 3/1992 | Rosenberg | 604/284 |
| 5,100,396 A | 3/1992 | Zamierowski | |
| 5,101,808 A | 4/1992 | Kobayashi et al. | |
| 5,106,362 A | 4/1992 | Gilman | |
| 5,106,629 A | 4/1992 | Cartmell | |
| 5,108,364 A * | 4/1992 | Takezawa et al. | 604/43 |
| 5,134,994 A | 8/1992 | Say | 128/200.24 |
| 5,135,518 A | 8/1992 | Vera | |
| 5,146,925 A | 9/1992 | Snow | |
| 5,147,338 A | 9/1992 | Lang | |
| 5,149,331 A | 9/1992 | Ferdman et al. | |
| 5,152,757 A | 10/1992 | Eriksson | |
| 5,160,322 A | 11/1992 | Scheremet | |
| 5,167,613 A | 12/1992 | Karami | |
| 5,167,622 A * | 12/1992 | Muto | 604/35 |
| 5,170,781 A | 12/1992 | Loomis | |
| 5,176,502 A | 1/1993 | Sanderson et al. | |
| 5,176,663 A | 1/1993 | Svedman | |
| 5,176,667 A | 1/1993 | DeBring | |
| 5,181,908 A * | 1/1993 | Bell | 604/24 |
| 5,189,609 A | 2/1993 | Tivig et al. | |
| 5,197,948 A * | 3/1993 | Ghodsian | 604/30 |
| 5,215,522 A | 6/1993 | Page et al. | 604/33 |
| 5,215,539 A | 6/1993 | Schoolman | |
| 5,224,929 A * | 7/1993 | Remiszewski | 604/30 |
| 5,228,431 A | 7/1993 | Giarretto | |
| 5,230,350 A | 7/1993 | Fentress | |
| 5,232,453 A | 8/1993 | Plass et al. | 604/180 |
| 5,238,654 A | 8/1993 | Nohl | |
| 5,249,121 A | 9/1993 | Baum et al. | |
| 5,256,418 A | 10/1993 | Kemp et al. | 424/423 |
| 5,261,893 A | 11/1993 | Zamierowski | |
| 5,263,922 A | 11/1993 | Sova | |
| 5,265,605 A | 11/1993 | Afflerbach | |
| 5,275,826 A | 1/1994 | Badylak et al. | 424/551 |
| 5,278,100 A | 1/1994 | Doan et al. | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley | |
| 5,298,015 A | 3/1994 | Komatsuzaki et al. | |
| 5,306,298 A | 4/1994 | Godley | |
| 5,314,409 A * | 5/1994 | Sarosiek et al. | 604/101.03 |
| 5,330,452 A | 7/1994 | Zook | |
| 5,335,651 A | 8/1994 | Foster | |
| 5,338,293 A * | 8/1994 | Jeppsson et al. | 604/29 |
| 5,342,293 A | 8/1994 | Zanger | |
| 5,342,301 A * | 8/1994 | Saab | 604/103.13 |
| 5,342,376 A | 8/1994 | Ruff | 606/151 |
| 5,344,415 A | 9/1994 | DeBusk | |
| 5,349,965 A | 9/1994 | McCarver | |
| 5,352,463 A | 10/1994 | Badylak et al. | 424/551 |
| 5,358,494 A * | 10/1994 | Svedman | 604/313 |
| 5,370,610 A * | 12/1994 | Reynolds | 604/43 |
| 5,372,821 A | 12/1994 | Badylak et al. | 424/551 |
| 5,374,254 A | 12/1994 | Buma | |
| 5,376,252 A | 12/1994 | Ekstrom et al. | |
| 5,380,280 A | 1/1995 | Peterson | |
| 5,395,315 A | 3/1995 | Griep | |
| 5,409,013 A * | 4/1995 | Clement | 600/566 |
| 5,413,788 A | 5/1995 | Edwards et al. | |
| 5,419,768 A | 5/1995 | Kayser | |
| 5,431,622 A | 7/1995 | Pyrozyk | |
| 5,437,622 A | 8/1995 | Carion | 602/57 |
| 5,437,651 A | 8/1995 | Todd et al. | |
| 5,439,452 A * | 8/1995 | McCarty | 604/248 |
| 5,445,604 A | 8/1995 | Lang | |
| 5,445,833 A | 8/1995 | Badylak et al. | 424/551 |
| 5,447,505 A | 9/1995 | Valentine et al. | |
| 5,449,383 A | 9/1995 | Chatelier et al. | 623/1 |
| 5,451,215 A | 9/1995 | Wolter | |
| 5,451,373 A | 9/1995 | Lewis et al. | |
| 5,478,333 A | 12/1995 | Asherman | |
| 5,484,420 A | 1/1996 | Russo | |
| 5,484,427 A | 1/1996 | Gibbons | |
| 5,484,428 A | 1/1996 | Drainville | |
| 5,487,889 A | 1/1996 | Eckert et al. | |
| 5,516,533 A | 5/1996 | Badylak et al. | 424/551 |
| 5,520,652 A | 5/1996 | Peterson | |
| 5,527,293 A | 6/1996 | Zamierowski | |
| 5,531,670 A | 7/1996 | Westby | |
| 5,533,981 A | 7/1996 | Mandro | |
| 5,534,346 A | 7/1996 | Robinson | |
| 5,540,668 A * | 7/1996 | Wilson et al. | 604/248 |
| 5,542,918 A | 8/1996 | Atkinson | |
| 5,549,584 A | 8/1996 | Gross | |
| 5,554,389 A | 9/1996 | Badylak et al. | 424/558 |
| 5,556,375 A | 9/1996 | Ewall | |
| 5,558,639 A | 9/1996 | Gangemi | |
| 5,573,784 A | 11/1996 | Badylak et al. | 424/551 |
| 5,578,022 A | 11/1996 | Scherson | |
| 5,578,662 A | 11/1996 | Bennett et al. | 524/54 |
| 5,607,388 A | 3/1997 | Ewall | |
| 5,621,035 A | 4/1997 | Lyles et al. | 524/404 |
| 5,624,418 A | 4/1997 | Shepard | |
| 5,628,735 A | 5/1997 | Skow | |
| 5,629,186 A | 5/1997 | Yasukawa et al. | 435/177 |
| 5,631,011 A | 5/1997 | Wadström | 424/400 |
| 5,635,201 A | 6/1997 | Fabo | 424/443 |
| 5,636,643 A | 6/1997 | Argenta | |
| 5,641,518 A | 6/1997 | Badylak et al. | 424/551 |
| 5,645,081 A | 7/1997 | Argenta | |
| 5,645,860 A | 7/1997 | Knapp et al. | 424/551 |
| 5,655,258 A | 8/1997 | Heintz | |
| 5,656,027 A | 8/1997 | Ellingboe | |
| 5,662,598 A | 9/1997 | Tobin | |
| 5,662,624 A | 9/1997 | Sundstrom et al. | |
| 5,662,625 A | 9/1997 | Westwood | |
| 5,669,892 A | 9/1997 | Keogh et al. | |
| 5,672,151 A | 9/1997 | Calderon-Garcidueñas | 602/21 |
| 5,672,152 A | 9/1997 | Mason | |
| 5,674,193 A | 10/1997 | Hayes | 604/28 |
| 5,678,564 A | 10/1997 | Lawrence | |
| 5,681,290 A | 10/1997 | Alexander | 604/180 |
| 5,690,815 A | 11/1997 | Krasnoff et al. | |
| 5,695,998 A | 12/1997 | Badylak et al. | 435/391 |
| 5,697,920 A | 12/1997 | Gibbons | |
| 5,711,969 A | 1/1998 | Patel et al. | 424/551 |
| 5,718,955 A | 2/1998 | McGuire | |
| 5,735,833 A | 4/1998 | Olson | |
| 5,738,656 A | 4/1998 | Wagner | 604/119 |
| 5,741,237 A | 4/1998 | Walker | |
| 5,749,842 A | 5/1998 | Cheong et al. | 602/41 |
| 5,753,267 A | 5/1998 | Badylak et al. | 424/551 |
| 5,755,791 A | 5/1998 | Whitson et al. | 623/15 |
| 5,759,570 A | 6/1998 | Arnold | |
| 5,762,640 A | 6/1998 | Kajiwara | |
| 5,762,966 A | 6/1998 | Knapp et al. | 424/551 |
| 5,780,281 A | 7/1998 | Yasukawa et al. | 435/176 |
| 5,782,871 A | 7/1998 | Fujiwara | |

| Patent No. | Kind | Date | Inventor | Class |
|---|---|---|---|---|
| 5,795,584 | A | 8/1998 | Totakura et al. | 424/426 |
| 5,800,383 | A | 9/1998 | Chandler et al. | 604/35 |
| 5,817,145 | A | 10/1998 | Augustine et al. | |
| 5,827,246 | A | 10/1998 | Bowen | |
| 5,827,296 | A | 10/1998 | Morris | |
| 5,855,619 | A | 1/1999 | Caplan et al. | 623/11 |
| 5,866,414 | A | 2/1999 | Badylak et al. | 435/325 |
| 5,881,723 | A | 3/1999 | Wallace et al. | |
| 5,891,111 | A * | 4/1999 | Ismael | 604/541 |
| 5,902,874 | A | 5/1999 | Roby et al. | 528/310 |
| 5,902,875 | A | 5/1999 | Roby et al. | 528/310 |
| 5,911,222 | A | 6/1999 | Lawrence | |
| 5,914,387 | A | 6/1999 | Roby et al. | 528/310 |
| 5,919,476 | A | 7/1999 | Fischer et al. | |
| 5,921,972 | A | 7/1999 | Skow | |
| 5,928,174 | A | 7/1999 | Gibbins | |
| 5,931,304 | A | 8/1999 | Hammond | 206/570 |
| 5,941,859 | A | 8/1999 | Lerman | |
| 5,942,496 | A | 8/1999 | Bonadio et al. | 514/44 |
| 5,947,914 | A | 9/1999 | Augustine | |
| 5,951,295 | A | 9/1999 | Lyles et al. | 433/228.1 |
| 5,954,680 | A | 9/1999 | Augustine | |
| 5,961,480 | A | 10/1999 | Augustine | |
| 5,962,427 | A | 10/1999 | Goldstein et al. | 514/44 |
| 5,964,721 | A | 10/1999 | Augustine | |
| 5,964,723 | A | 10/1999 | Augustine | |
| 5,986,163 | A | 11/1999 | Augustine | |
| 5,997,568 | A | 12/1999 | Liu | 606/228 |
| 6,010,527 | A | 1/2000 | Augustine et al. | |
| 6,013,048 | A | 1/2000 | Podany et al. | 604/22 |
| 6,017,493 | A | 1/2000 | Cambron et al. | |
| 6,039,724 | A | 3/2000 | Seifert | |
| 6,045,518 | A | 4/2000 | Augustine | |
| 6,045,541 | A | 4/2000 | Matsumoto | |
| 6,051,747 | A | 4/2000 | Lindqvist et al. | |
| 6,056,730 | A | 5/2000 | Greter | |
| 6,071,254 | A | 6/2000 | Augustine | |
| 6,071,267 | A * | 6/2000 | Zamierowski | 604/289 |
| 6,071,304 | A | 6/2000 | Augustine et al. | |
| 6,080,189 | A | 6/2000 | Augustine et al. | |
| 6,080,243 | A | 6/2000 | Insley | |
| 6,093,160 | A | 7/2000 | Augustine et al. | |
| 6,093,230 | A | 7/2000 | Johnson | |
| 6,095,992 | A | 8/2000 | Augustine | |
| 6,099,567 | A | 8/2000 | Badylak et al. | 623/13 |
| 6,110,197 | A | 8/2000 | Augustine | |
| 6,113,561 | A | 9/2000 | Augustine | |
| 6,117,111 | A | 9/2000 | Fleischmann | |
| 6,135,116 | A | 10/2000 | Vogel et al. | |
| 6,142,982 | A | 11/2000 | Hunt | |
| 6,143,945 | A | 11/2000 | Augustine et al. | |
| 6,149,614 | A | 11/2000 | Dunshee et al. | |
| 6,171,344 | B1 | 1/2001 | Atala | 623/23.64 |
| 6,174,306 | B1 | 1/2001 | Fleischmann | |
| 6,203,563 | B1 | 3/2001 | Fernandez | |
| 6,206,931 | B1 | 3/2001 | Cook et al. | 623/23.75 |
| 6,207,875 | B1 | 3/2001 | Lindqvist et al. | |
| 6,213,965 | B1 | 4/2001 | Augustine et al. | |
| 6,213,966 | B1 | 4/2001 | Augustine | |
| 6,217,535 | B1 | 4/2001 | Augustine | |
| 6,235,009 | B1 | 5/2001 | Skow | |
| 6,235,047 | B1 | 5/2001 | Augustine et al. | |
| 6,241,697 | B1 | 6/2001 | Augustine | |
| 6,241,698 | B1 | 6/2001 | Augustine | |
| 6,241,747 | B1 | 6/2001 | Ruff | 606/216 |
| 6,244,311 | B1 | 6/2001 | Hand et al. | |
| 6,244,698 | B1 | 6/2001 | Chino et al. | |
| 6,248,084 | B1 | 6/2001 | Augustine et al. | |
| 6,254,557 | B1 | 7/2001 | Augustine et al. | |
| 6,254,580 | B1 | 7/2001 | Svedman | |
| 6,259,067 | B1 | 7/2001 | Faries, Jr. et al. | |
| 6,264,622 | B1 | 7/2001 | Augustine | |
| 6,264,979 | B1 | 7/2001 | Svedman | |
| 6,267,740 | B1 | 7/2001 | Augustine | |
| 6,283,931 | B1 | 9/2001 | Augustine | |
| 6,284,941 | B1 | 9/2001 | Cox et al. | |
| 6,287,316 | B1 | 9/2001 | Agarwal et al. | 606/151 |
| 6,290,685 | B1 | 9/2001 | Insley et al. | |
| 6,293,917 | B1 | 9/2001 | Augustine et al. | |
| 6,325,798 | B1 | 12/2001 | Edwards et al. | 606/41 |
| 6,345,623 | B1 | 2/2002 | Heaton | |
| 6,364,853 | B1 | 4/2002 | French et al. | 604/35 |
| 6,394,142 | B1 * | 5/2002 | Woelfel et al. | 138/115 |
| 6,398,767 | B1 | 6/2002 | Fleischmann | |
| 6,410,427 | B1 | 6/2002 | Hu | 438/655 |
| 6,440,427 | B1 | 8/2002 | Wadström | 424/400 |
| 6,458,109 | B1 * | 10/2002 | Henley et al. | 604/304 |
| 6,471,685 | B1 * | 10/2002 | Johnson | 604/890.1 |
| 6,472,581 | B1 | 10/2002 | Muramatsu | |
| 6,488,643 | B1 | 12/2002 | Tumey et al. | 602/13 |
| 6,491,682 | B2 | 12/2002 | Paderni | |
| 6,491,693 | B1 | 12/2002 | Lytinas | |
| 6,493,568 | B1 | 12/2002 | Bell et al. | 600/323 |
| 6,500,112 | B1 | 12/2002 | Khouri | |
| 6,520,982 | B1 | 2/2003 | Boynton | |
| 6,553,998 | B2 | 4/2003 | Heaton | |
| 6,557,704 | B1 | 5/2003 | Randolph | |
| 6,559,773 | B1 | 5/2003 | Berry | |
| 6,599,277 | B2 | 7/2003 | Neubert | |
| 6,626,891 | B2 | 9/2003 | Ohmstede | |
| 6,638,270 | B2 | 10/2003 | Johnson | |
| 6,648,862 | B2 | 11/2003 | Watson | |
| 6,663,349 | B1 | 12/2003 | Discenzo et al. | |
| 6,685,681 | B2 * | 2/2004 | Lockwood et al. | 604/305 |
| 6,691,047 | B1 | 2/2004 | Fredericks | |
| 6,695,823 | B1 | 2/2004 | Lina et al. | |
| 6,695,824 | B2 | 2/2004 | Howard | |
| 6,719,779 | B2 | 4/2004 | Daoud | |
| 6,749,592 | B2 | 6/2004 | Lord | |
| 6,752,794 | B2 * | 6/2004 | Lockwood et al. | 604/313 |
| 6,755,807 | B2 * | 6/2004 | Risk et al. | 604/319 |
| 6,764,462 | B2 | 7/2004 | Risk, Jr. | |
| 6,767,334 | B1 | 7/2004 | Randolph | |
| 6,800,074 | B2 | 10/2004 | Henley et al. | |
| 6,814,079 | B2 | 11/2004 | Heaton | |
| 6,824,533 | B2 | 11/2004 | Risk, Jr. | |
| 6,855,135 | B2 * | 2/2005 | Lockwood et al. | 604/313 |
| 6,856,821 | B2 | 2/2005 | Johnson | |
| 6,936,037 | B2 | 8/2005 | Bubb et al. | |
| 6,951,553 | B2 | 10/2005 | Bubb | |
| 6,966,889 | B2 * | 11/2005 | Saab | 604/96.01 |
| 6,979,324 | B2 * | 12/2005 | Bybordi et al. | 604/313 |
| 6,994,702 | B1 | 2/2006 | Johnson | |
| 7,004,915 | B2 | 2/2006 | Boynton et al. | |
| 7,022,113 | B2 | 4/2006 | Lockwood et al. | |
| 7,070,584 | B2 | 7/2006 | Johnson | |
| 7,077,832 | B2 | 7/2006 | Fleischmann | |
| 7,108,683 | B2 | 9/2006 | Zamierowski | |
| 7,117,869 | B2 | 10/2006 | Heaton | |
| 7,128,735 | B2 | 10/2006 | Weston | |
| 7,144,390 | B1 | 12/2006 | Hannigan et al. | |
| 7,195,624 | B2 * | 3/2007 | Lockwood et al. | 604/543 |
| 7,245,291 | B2 | 7/2007 | Sharif et al. | |
| 7,276,051 | B1 * | 10/2007 | Henley et al. | 604/304 |
| 7,338,482 | B2 * | 3/2008 | Lockwood et al. | 604/543 |
| 7,381,211 | B2 | 6/2008 | Zamierowski | 606/215 |
| 7,422,576 | B2 | 9/2008 | Boynton et al. | 607/104 |
| 7,524,286 | B2 | 4/2009 | Johnson | 600/309 |
| 7,534,927 | B2 | 5/2009 | Lockwood et al. | 602/46 |
| 2001/0029956 | A1 | 10/2001 | Argenta et al. | |
| 2001/0034499 | A1 | 10/2001 | Sessions et al. | |
| 2001/0043943 | A1 | 11/2001 | Coffey | |
| 2001/0052681 | A1 | 12/2001 | Deavila | 280/47.19 |
| 2002/0065494 | A1 | 5/2002 | Lockwood et al. | |
| 2002/0077661 | A1 | 6/2002 | Saadat | 606/221 |
| 2002/0082567 | A1 | 6/2002 | Lockwood et al. | 604/313 |
| 2002/0082668 | A1 | 6/2002 | Ingman | |
| 2002/0085952 | A1 | 7/2002 | Ellingboe et al. | 422/45 |
| 2002/0115951 | A1 | 8/2002 | Norstrem et al. | 602/27 |
| 2002/0115952 | A1 | 8/2002 | Johnson et al. | |
| 2002/0120185 | A1 | 8/2002 | Johnson | 600/345 |
| 2002/0143286 | A1 | 10/2002 | Tumey | |
| 2002/0161317 | A1 * | 10/2002 | Risk et al. | 602/2 |
| 2002/0183702 | A1 * | 12/2002 | Henley et al. | 604/305 |
| 2002/0193723 | A1 | 12/2002 | Batdorf, Sr. et al. | |
| 2003/0032951 | A1 | 2/2003 | Rittman, III et al. | |
| 2003/0077311 | A1 | 4/2003 | Vyakarnam et al. | 435/41 |
| 2003/0093041 | A1 | 5/2003 | Risk et al. | |

| Publication | Date | Name |
|---|---|---|
| 2003/0143352 A1* | 7/2003 | Yang et al. .................... 428/36.9 |
| 2003/0208149 A1 | 11/2003 | Coffey |
| 2003/0219469 A1 | 11/2003 | Johnson et al. |
| 2003/0225441 A1 | 12/2003 | Boynton et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0167482 A1 | 8/2004 | Watson |
| 2004/0225208 A1 | 11/2004 | Johnson |
| 2004/0243073 A1* | 12/2004 | Lockwood et al. ............ 604/313 |
| 2004/0249353 A1 | 12/2004 | Risks, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0033197 A1 | 2/2005 | Cottler |
| 2005/0065484 A1 | 3/2005 | Watson, Jr. |
| 2005/0070858 A1 | 3/2005 | Lockwood et al. |
| 2005/0085795 A1 | 4/2005 | Lockwood et al. |
| 2005/0090787 A1* | 4/2005 | Risk et al. ..................... 604/305 |
| 2005/0131327 A1* | 6/2005 | Lockwood et al. ............. 602/41 |
| 2005/0177190 A1 | 8/2005 | Zamierowski |
| 2005/0182445 A1 | 8/2005 | Zamierowski |
| 2005/0182446 A1 | 8/2005 | DeSantis ...................... 606/222 |
| 2005/0234485 A1 | 10/2005 | Seegert et al. |
| 2005/0234510 A1 | 10/2005 | Zamierowski |
| 2005/0240220 A1 | 10/2005 | Zamierowski |
| 2005/0283105 A1 | 12/2005 | Heaton et al. |
| 2006/0015087 A1 | 1/2006 | Risk, Jr. et al. |
| 2006/0029650 A1 | 2/2006 | Coffey |
| 2006/0029675 A1 | 2/2006 | Ginther |
| 2006/0041247 A1 | 2/2006 | Petrosenko et al. |
| 2006/0079852 A1 | 4/2006 | Bubb et al. |
| 2006/0129137 A1 | 6/2006 | Lockwood et al. |
| 2006/0149170 A1 | 7/2006 | Boynton et al. |
| 2006/0149171 A1 | 7/2006 | Vogel et al. |
| 2006/0173253 A1 | 8/2006 | Ganapathy et al. |
| 2006/0189910 A1 | 8/2006 | Johnson et al. |
| 2006/0213527 A1 | 9/2006 | Argenta et al. |
| 2007/0005028 A1 | 1/2007 | Risk, Jr. et al. |
| 2007/0014837 A1 | 1/2007 | Johnson et al. |
| 2007/0021697 A1 | 1/2007 | Ginther et al. |
| 2007/0021698 A1 | 1/2007 | Fleischmann |
| 2007/0032778 A1 | 2/2007 | Heaton et al. |
| 2007/0038172 A1 | 2/2007 | Zamierowski |
| 2007/0156104 A1 | 7/2007 | Lockwood et al. |
| 2007/0233022 A1 | 10/2007 | Henley et al. .................. 604/304 |
| 2009/0082740 A1 | 3/2009 | Lockwood et al. ............. 602/41 |
| 2010/0063483 A1* | 3/2010 | Adahan .......................... 604/543 |

FOREIGN PATENT DOCUMENTS

| | | |
|---|---|---|
| AU | 745271 | 4/1999 |
| AU | 755496 | 2/2002 |
| CA | 1127488 | 7/1982 |
| CA | 2005436 | 6/1990 |
| CA | 2303085 | 3/1999 |
| DE | 372727 | 3/1923 |
| DE | 2640413 A1 | 3/1978 |
| DE | 2809828 A1 | 9/1978 |
| DE | 3102674 A1 | 9/1982 |
| DE | 3539533 A1 | 5/1987 |
| DE | 40 12 232 | 10/1991 |
| DE | 4111122 A1 | 4/1993 |
| DE | 4306478 A1 | 9/1994 |
| DE | 29504378 U1 | 10/1995 |
| DE | 29715634 | 11/1997 |
| DE | 19722075 C1 | 10/1998 |
| DK | 64055 | 10/1945 |
| EP | 0 100 148 A1 | 2/1984 |
| EP | 0117632 A2 | 9/1984 |
| EP | 0 161 865 A2 | 11/1985 |
| EP | 0 358 302 A2 | 3/1990 |
| EP | 0424165 A1 | 4/1991 |
| EP | 0485657 A1 | 5/1992 |
| EP | 0547496 A1 | 6/1993 |
| EP | 0853950 A1 | 7/1998 |
| EP | 0777504 B1 | 10/1998 |
| EP | 0880953 A2 | 12/1998 |
| EP | 1088569 A2 | 4/2001 |
| EP | 1100574 | 5/2001 |
| EP | 1 190 732 A1 | 3/2002 |
| EP | 1 018 967 B1 | 8/2004 |
| EP | 1726276 A2 | 11/2006 |
| FR | 500253 | 3/1920 |
| FR | 1303238 | 7/1962 |
| GB | 3090 | 0/1902 |
| GB | 641061 | 8/1950 |
| GB | 692578 | 6/1953 |
| GB | 1549756 | 8/1979 |
| GB | 1584772 | 2/1981 |
| GB | 2195255 A | 4/1988 |
| GB | 2197789 A | 6/1988 |
| GB | 2220357 A | 1/1990 |
| GB | 2235877 A | 3/1991 |
| GB | 2307180 A | 5/1997 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 6/2000 |
| GB | 2351025 A | 12/2000 |
| GB | 2356148 A | 5/2001 |
| HU | 47035 | 1/1989 |
| HU | 199304 B | 1/1989 |
| HU | 51150 | 4/1990 |
| HU | 205557 B | 4/1990 |
| HU | 76361 | 8/1997 |
| HU | 215563 B | 8/1997 |
| HU | 1666 | 12/1999 |
| JP | 57-177758 | 11/1982 |
| JP | 4-129536 | 4/1992 |
| JP | 06327761 | 11/1994 |
| SG | 71559 | 4/2002 |
| SU | 58741 | 1/1978 |
| SU | 1268175 A1 | 11/1986 |
| WO | WO 80/02182 | 10/1980 |
| WO | WO 87/04626 | 8/1987 |
| WO | 89/04158 | 5/1989 |
| WO | WO 90/10424 | 9/1990 |
| WO | 91/00718 | 1/1991 |
| WO | 91/08793 | 6/1991 |
| WO | 91/16030 | 10/1991 |
| WO | 92/12750 | 8/1992 |
| WO | 92/19313 | 11/1992 |
| WO | 92/20299 | 11/1992 |
| WO | 93/09715 | 5/1993 |
| WO | 93/09727 | 5/1993 |
| WO | 94/00090 | 5/1994 |
| WO | 94/20041 | 9/1994 |
| WO | 96/05873 | 2/1996 |
| WO | 96/15745 | 5/1996 |
| WO | 97/18007 | 5/1997 |
| WO | WO 98/02205 | 1/1998 |
| WO | 98/38944 | 9/1998 |
| WO | 99/01173 | 1/1999 |
| WO | 99/13793 | 3/1999 |
| WO | 99/23990 | 5/1999 |
| WO | 99/59816 | 11/1999 |
| WO | 00/07653 | 2/2000 |
| WO | 00/15277 | 3/2000 |
| WO | 00/21586 | 4/2000 |
| WO | 00/26100 | 5/2000 |
| WO | WO 00/28890 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 A1 | 5/2001 |
| WO | 01/37922 A2 | 5/2001 |
| WO | 01/49233 A1 | 7/2001 |
| WO | 01/85248 A1 | 11/2001 |
| WO | 01/89431 | 11/2001 |
| WO | 01/89431 A1 | 11/2001 |
| WO | 02/38091 | 5/2002 |

| | | |
|---|---|---|
| WO | WO 02/43634 | 6/2002 |
| WO | 03/005943 A3 | 1/2003 |
| WO | 03/045492 A1 | 6/2003 |
| WO | WO 03/057071 | 7/2003 |
| WO | WO 03/057307 | 7/2003 |
| WO | WO 03/101508 | 12/2003 |

OTHER PUBLICATIONS

Davydov, et al., Vestn. Khir., Sep. 1988 * "Vacuum Therapy in the Treatment of Acute Suppurative Diseases of Soft Tissues and Suppurative Wounds" (English translation by R. McElroy Translation Co., Austin, Texas).

Davydov, et al., Khirurgiia, Jun. 1990 * "Pathogenic Mechanism of the Effect of Vacuum Therapy on the Course of the Wound Process" (English translation by R. McElroy Translation Co., Austin, Texas).

Davydov, et al., Vestn. Khir., Nov. 1986 * "Vacuum Therapy in the Treatment of Suppurative Lactation Mastitis" (English translation by R. McElroy Translation Co., Austin, Texas).

Davydov, et al., Vestn. Khir., Oct. 1988 * "Bacteriological and Cytological Evaluation of the Vacuum Therapy of Suppurative Wounds" (English translation by R. McElroy Translation Co., Austin, Texas).

Davydov, et al., Vestn. Khir., Mar. 1990 * "Basis of the Use of Forced Early Secondary Suture in the Treatment of Suppurative Wounds by the Vacuum Therapy Method" (English translation by R. McElroy Translation Co., Austin, Texas).

Mirazimov, et al., Ortop Travmatol Protez., Oct. 1966 * "Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (English translation by R. McElroy Translation Co., Austin, Texas).

Jeter, et al., Chronic Wound Care; 27: pp. 240*246 * "Managing Draining Wounds and Fistulae: New and Established Methods".

Mulder, et al., Wound Healing Publications 1991 * "Clinicians' Pocket Guide to Chronic Wound Repair".

Valenta, AIN Apr. 1994; pp. 44*45 * "Using the Vacuum Dressing Alternative for Difficult Wounds".

Wolthuis, et al., Physiological Reviews Jul. 1974; vol. 54, No. 3, pp. 566*595—"Physiological Effects of Locally Applied Reduced Pressure in Man".

Fleischmann, WundForum Special IHW 1994; pp. 54*55 * "Vacuum Sealing for Treatment of Problematical Wounds" (English translation provided).

Bucalo, et al., Wound Repair and Regeneration; Jul.*Sep. 1993; pp. 181*186—"Inhibition of Cell Proliferation by Chronic Wound Fluid" by Chronic Wound Fluid.

Olenius, et al., Plastic and Reconstructive Surgery Feb. 1993: pp. 213*215—"Mitotic Activity in Expanded Human Skin".

Viljanto, et al., Br. J. Surg. 1976; vol. 63: pp. 427*430 * "Local Hyperalimentation of Open Wounds".

Dunlop, et al., Br. J. Surg. May 1990; vol. 77: pp. 562*563 * "Vacuum Drainage of Groin Wounds after Vascular Surgery: A Controlled Trial".

** Comment*Ruckley et al. (or Dunlap), Apr. 1991, pp. 505*506 on "Vacuum Drainage of Groin Wounds after Vascular Surgery".

Landis, et al., Alternate Suction and Pressure, pp. 925*961 * "The Effects of Alternative Suction and Pressure on Blood Flow to the Lower Extremities".

Morykwas, et al., Extracellular Matrix and Healing 1993; pp. 800 * "Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97 * "Nonsurgical Modalities to Enhance Healing and Care of Soft Tissue Wounds"; Feb. 11, 1999; 16 pages.

Chariker, et al., Contemporary Surgery Jun. 1989; vol. 34: pp. 59*63 * "Effective Management of Incisional and Cutaneous Fistulae with Closed Suction Wound Drainage".

Tittel, et al., Eingag und Annahme des Manuskripts Jan. 7, 1987; pp. 104*107 * "New Standards in Postoperative Wound Drainage".

Genecov, et al., Annals of Plastic Surgery Mar. 1998; vol. 40, No. 3: pp. 219-225—"A Controlled Subatmospheric Pressure Dressing Increases the Rate of Skin Graft Donor Site Reepithelialization".

Morykwas, et al., Annals of Plastic Surgery Jun. 1997; vol. 38, No. 6: pp. 553-562 * "Vacuum-Assisted Closure: A New Method for Wound Control and Treatment: Animal Studies and Basic Foundation".

Argenta, et al., Annals of Plastic Surgery Jun. 1997; vol. 38, No. 6: pp. 563-577 * "Vacuum-Assisted Closure: a New Method for Wound Control and Treatment: Clinical Experience".

Patent Application and Drawings * "Method of Treating Tissue Damage and Apparatus for Same", consisting of 28 pages.

Patent Application and Drawings * "The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499*502 * "A New Dressing Method for Free Skin Grafting in Hands".

Medical Industry Week * article "KCI Offers New Treatment for Non*Healing Wounds"; 1 page.

Nakayama, et al., Plast. Reconstr. Surg., Dec. 1990.; vol. 86, No. 6: pp. 1216-1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).

Teder, et al., J. Invest. Surg.1990; vol. 3: pp. 399-407—"Continuous Wound Irrigation in the Pig".

Wood, et al., Br. J. of Surg.1977; vol. 64: pp. 554-557—"Foam Elastomer Dressing in the Management of Open Granulating Wounds: Experience with 250 Patients".

Neumann, et al., J. of Biomed. Materials Research 1981, vol. 15: pp. 9-18—"Gelatin-Based Sprayable Foam as a Skin Substitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta Physiol. Scand. 1989, vol. 136: pp. 403-409— "Transmission of Externally Applied Negative Pressure to the Underlying Tissue. A Study on the Upper Arm of Man".

Brochure * Aeros * Instavac Aspirator; 1 page.

Brochure Pleur*evac Adult*Pediatric*Non*Metered Disposable "3*Bottle" Unit, A-4000; 6 pages.

Brochure * Hiblow Air Pump; 1 page.

Brochure * Aeros * Care*E*Vac; 2 pages.

One page brochure * Aeros * Mobivacll.

Brochure/Instruction Manual—Creative Medical Laboratories, Inc.—TUGS (Transportable Universal Gradient Suction) System.

Brochure—Wells Johnson Company—Point 5 Aspirator; 2 pages.

Brochure—Microtek Heritage, Inc.—The Wound-Evac ET, Closed Wound Suction System; 4 pages.

Brochure—KCI—The V.A.C. (Vacuum Assisted Closure), Nov. 5, 1998; 7 pages.

Brochure—Augustine Medical, Warm-Up Active Wound Therapy Wound Covers, 1999; 3 pages.

Brochure—Series 55—Emerson Post-Operative Suction Pumps; 1 page.

Brochure-13 Emerson Transport Suction Unit; 1 page.

Office Action dated Jun. 9, 2006 U.S. Appl. No. 10/496,623.

International Search Report dated Jun. 30, 2003 for Application No. PCT/US02/41228.

Supplementary European Search Report, issued in European Application No. EP 02 79 4392, mailed Jun. 5, 2009.

"Jump-Start Wound Healing with Oasis," Wounds, Special Supplement, 13(2):1-28, 2001.

"Oasis™ Wound Dressing," SIS™ Technology, pp. 1-4, Sep. 2001.

"Surgisis™ Soft-Tissue Graft," SIS™ Technology, pp. 1-4, Sep. 2001.

Brochure—"Cavi-Care," *Smith & Nephew*, 2000.
Brochure—Healthpoint® Oasis® Wound Matrix, *Cook Biotech Incorporated*, 2003.
Fourth SIS-ECM Symposium, Phoenix, Arizona, Dec. 6-7, 2002.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Letter and Memo reporting Office Action issued in Mexican Application No. PA/a/2001/001124, mailed Jul. 13, 2004.
McCarty, "Cook Incorporated forms dedicated tissue engineered products group," *Cook® Online, News and Media Information*, 2000.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.

Office Action issued in U.S. Appl. No. 11/230,988, mailed Oct. 3, 2008.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
PCT Declaration of Non-Establishment of International Search Report issued in International Application No. PCT/US2003/17099, mailed Nov. 7, 2003.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus, First Edition (v 1.3.1), 2007.
Search Report issued in Hungarian Application No. P0103545, mailed Oct. 29, 2001.
Search Report issued in Hungarian Application No. P0500055, mailed May 3, 2005.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Supplementary Search Report issued in European Application No. 08010957.2, mailed Aug. 27, 2008.
Arnljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96.
Blackburn II et al.; "Negative-pressure dressings as a bolster for skin grafts," *Annals of Plastic Surgery*, 40(5):453-457, 1998.
Chinn and Burns, "Closed wound suction drainage," *The Journal of Foot Surgery*, 24(1):76-81, 1985.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Greer et al., "The use of subatmospheric pressure dressing therapy to close lymphocutaneous fistulas of the groin," *British Journal of Plastic Surgery*, 53(6):484-487, 2000.
Johnson, "An improved technique for skin graft placement using a suction drain," *Surgery, Gynecology, and Obstetrics*, 159(6):584-585, 1984.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," *Journal of Cardiovascular Surgery*, 31:634-639, 1990.
Masters, "Reliable, inexpensive and simple suction dressings," Letter to the Editor, *British Journal of Plastic Surgery*, Elsevier Science/The British Association of Plastic Surgeons, UK, 51(3):267, 1998.
Mendez-Eastman, "When wounds won't heal," *RN*, 61(1):20-24, 1998.
Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/509,137, mailed Dec. 20, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Jan. 10, 2007.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 10, 2007.
Office Action issued in U.S. Appl. No. 10/524,957, mailed Aug. 3, 2009.

Office Action issued in U.S. Appl. No. 10/524,957, mailed Sep. 30, 2008.
Office Action issued in U.S. Appl. No. 11/515,983, mailed May 11, 2009.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Orringer et al., "Management of wounds in patients with complex enterocutaneous fistulas," *Surgery, Gynecology & Obstetrics*, 165:79-80, 1987.
PCT International Preliminary Examination Report issued in International Application No. PCT/GB96/02802, mailed Jan. 15, 1998.
PCT International Search Report issued in International Application No. PCT/GB98/02713, mailed Jan. 8, 1999.
PCT International Search Report issued in International Application No. PCT/GB95/01983, mailed Nov. 23, 1995.
PCT International Search Report issued in International Application No. PCT/GB96/02802, mailed Apr. 29, 1997.
PCT Written Opinion issued in International Application No. PCT/GB96/02802, mailed Sep. 3, 1997.
PCT Written Opinion issued in International Application No. PCT/GB98/02713, mailed Jun. 8, 1999.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
Schein et al., "The 'Sandwich Technique' in the management of the open abdomen," *British Journal of Surgery*, 73:369-370, 1986.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary European Search Report, issued in European Application No. EP 02 79 4388, mailed Jul. 8, 2009.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Tennant, "The use of hypermia in the postoperative treatment of lesions of the extremities and thorax," *Journal of the American Medical Association*, 64:1548-1549, 1915.
Tribble, "An improved sump drain-irrigation device of simple construction," *Archives of Surgery*, 105(3):511-513, 1972.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164, 1986.
Advisory Action issued in U.S. Appl. No. 10/885,431, mailed Dec. 8, 2009.
Advisory Action issued in U.S. Appl. No. 11/515,983, mailed Feb. 1, 2010.
Advisory Action issued in U.S. Appl. No. 11/761,066, mailed Feb. 16, 2010.
Decision on Appeal issued in U.S. Appl. No. 10/276,778, mailed Mar. 6, 2010.
Decision on Appeal issued in U.S. Appl. No. 11/242,543, mailed Mar. 5, 2010.
Definition of "pore," provided by Merriam-Webster Online Dictionary, printed Apr. 5, 2010.
Definition of "porous," provided by Merriam-Webster Online Dictionary, printed Apr. 5, 2010.
Office Action issued in U.S. Appl. No. 10/509,137, mailed Apr. 9, 2010.
Office Action issued in U.S. Appl. No. 10/524,957, mailed Feb. 25, 2010.
Office Action issued in U.S. Appl. No. 10/664,535, mailed Dec. 15, 2009.
Office Action issued in U.S. Appl. No. 11/051,283, mailed Feb. 25, 2010.
Office Action issued in U.S. Appl. No. 11/515,983, mailed Nov. 20, 2009.
Office Action issued in U.S. Appl. No. 11/761,066, mailed Dec. 9, 2009.
Office Action issued in Canadian Application No. 2,481,016, mailed Jun. 15, 2010.
Office Action issued in Japanese Application No. 2001-539532, mailed May 11, 2010 (and English language translation thereof).
Office Action issued in U.S. Appl. No. 10/524,957, mailed Jul. 26, 2010.
Advisory Action issued in U.S. Appl. No. 10/509,137, mailed Jun. 24, 2010.
Advisory Action issued in U.S. Appl. No. 11/051,283, mailed May 5, 2010.
Communication of Notice of Opposition issued in European Application No. 07001838.7, mailed Apr. 28, 2010 (and copy of Opposition).
Notice of Allowance issued in U.S. Appl. No. 10/276,778, mailed May 21, 2010.
Notice of Allowance issued in U.S. Appl. No. 10/664,535, mailed Jun. 2, 2010.
Notice of Allowance issued in U.S. Appl. No. 10/885,431, mailed Mar. 22, 2010.
Notice of Allowance issued in U.S. Appl. No. 11/761,066, mailed May 13, 2010.
Office Action issued in Japanese Application No. 2004-508861, mailed Feb. 16, 2010 (and English language translation thereof).
Office Action issued in U.S. Appl. No. 11/230,988, mailed May 26, 2010.
Office Action issued in U.S. Appl. No. 11/515,983, mailed May 7, 2010.
Supplemental Notice of Allowability issued in U.S. Appl. No. 10/885,431, mailed Apr. 22, 2010.
Notice of Allowance issued in U.S. Appl. No. 10/276,778, mailed Sep. 7, 2010.
Notice of Allowance issued in U.S. Appl. No. 10/524,957, mailed Oct. 14, 2010.
Notice of Allowance issued in U.S. Appl. No. 10/664,535, mailed Sep. 9, 2010.
Notice of Allowance issued in U.S. Appl. No. 11/242,543, mailed Sep. 27, 2010.
Office Action issued in European Application No. 01 998 292.5, mailed May 7, 2010.
Office Action issued in U.S. Appl. No. 11/051,283, mailed Oct. 15, 2010.
Office Action issued in U.S. Appl. No. 11/230,988, mailed Oct. 15, 2010.
Office Action issued in U.S. Appl. No. 11/515,983, mailed Oct. 5, 2010.
Response to Opposition submitted in European Patent No. EP 1 772 160, filed Sep. 29, 2010.
Notice of Allowance issued in U.S. Appl. No. 11/684,989, mailed Nov. 8, 2010.
Office Action issued in European Application No. 02 794 397.6, mailed Oct. 12, 2010.
Office Action issued in Japanese Application No. 2008-007788, mailed Oct. 5, 2010, and English language translation thereof.

* cited by examiner

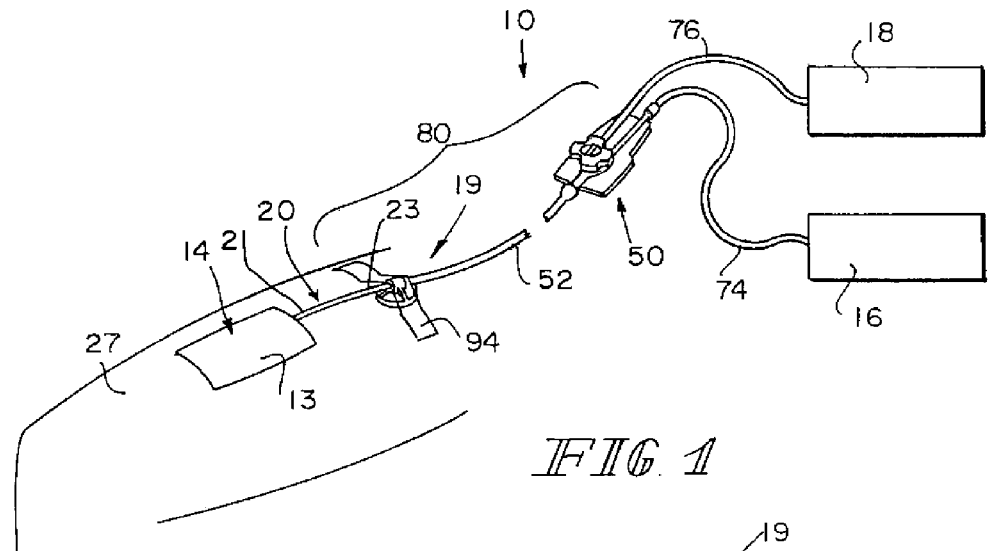
FIG. 1
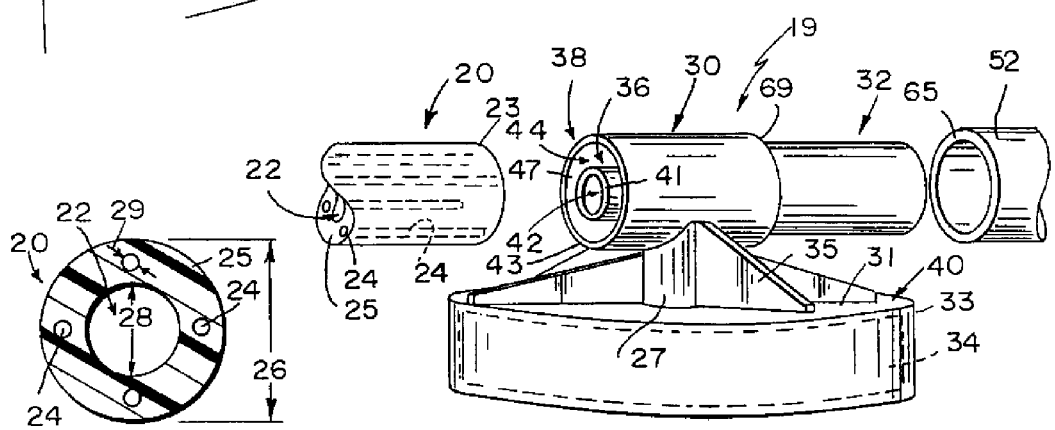
FIG. 4
FIG. 2
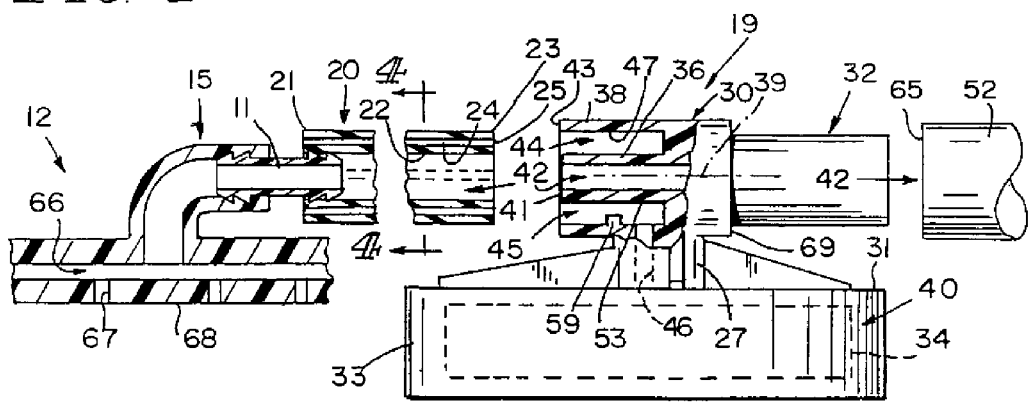
FIG. 3

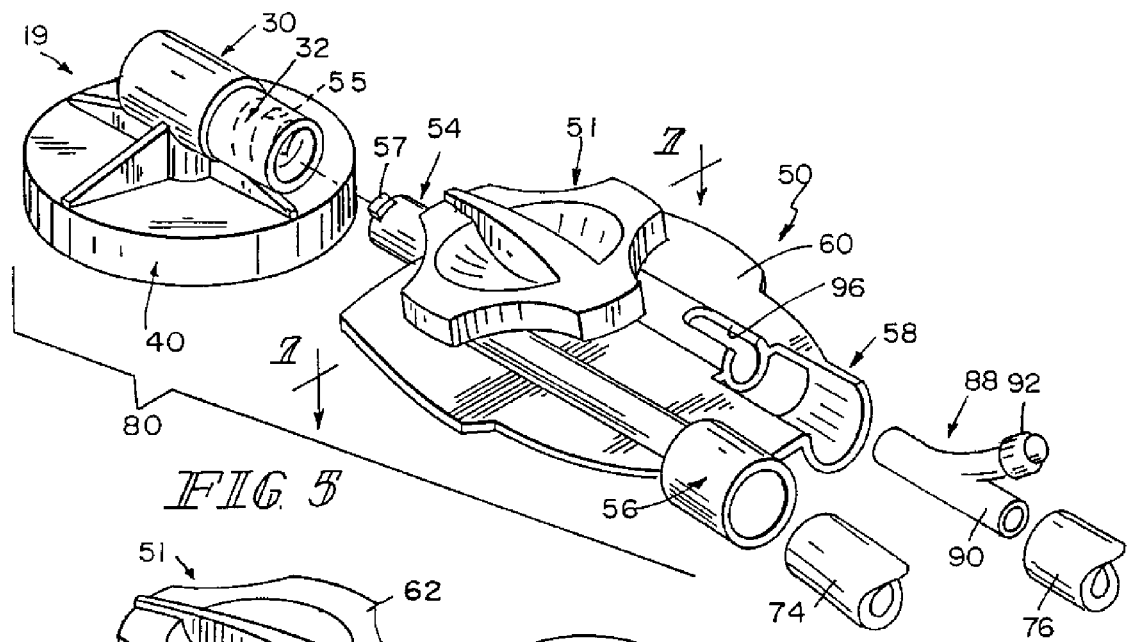
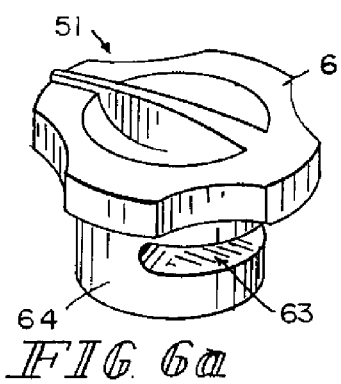
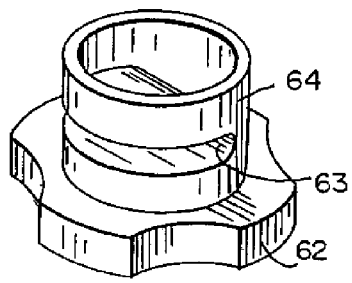
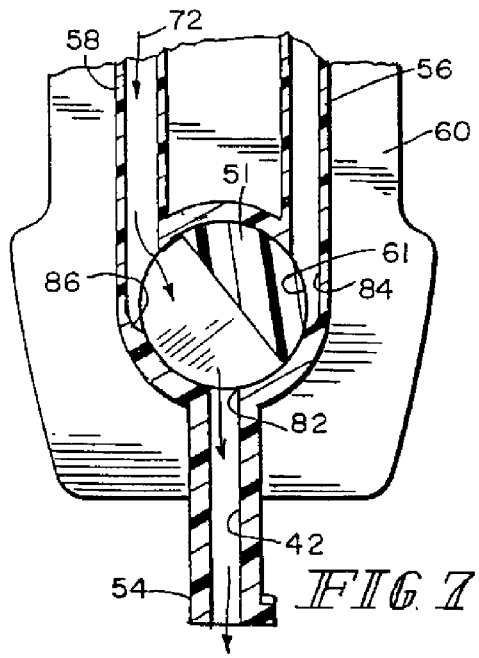
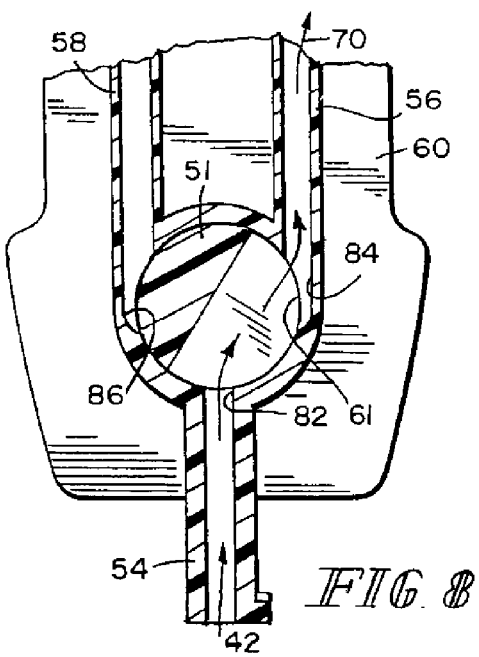

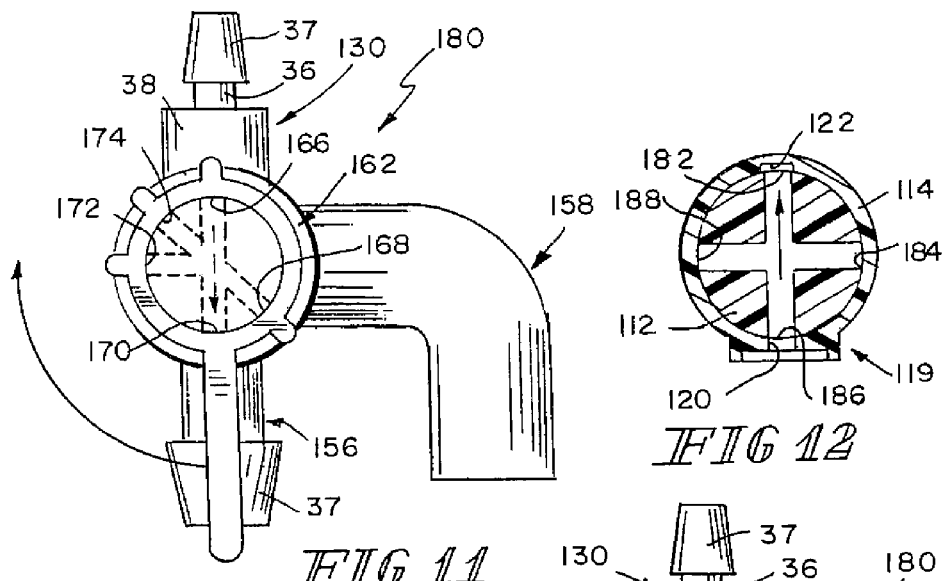
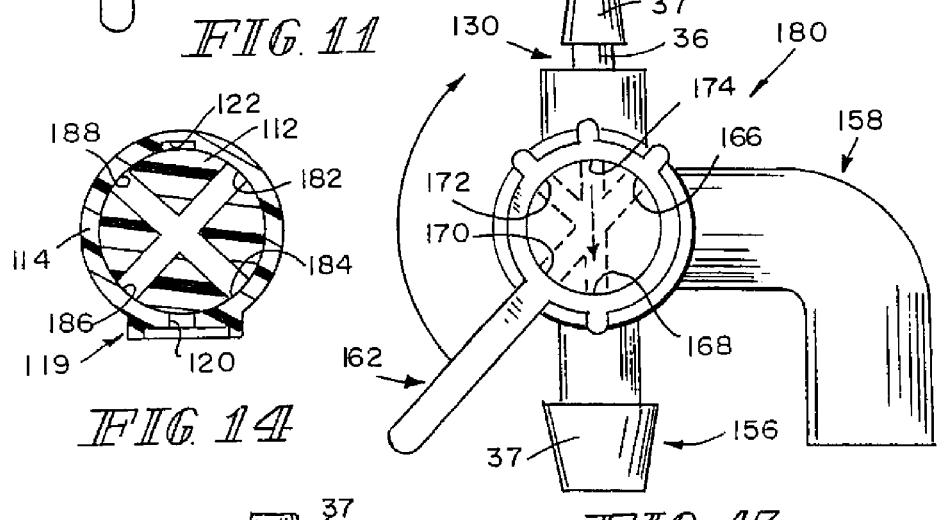
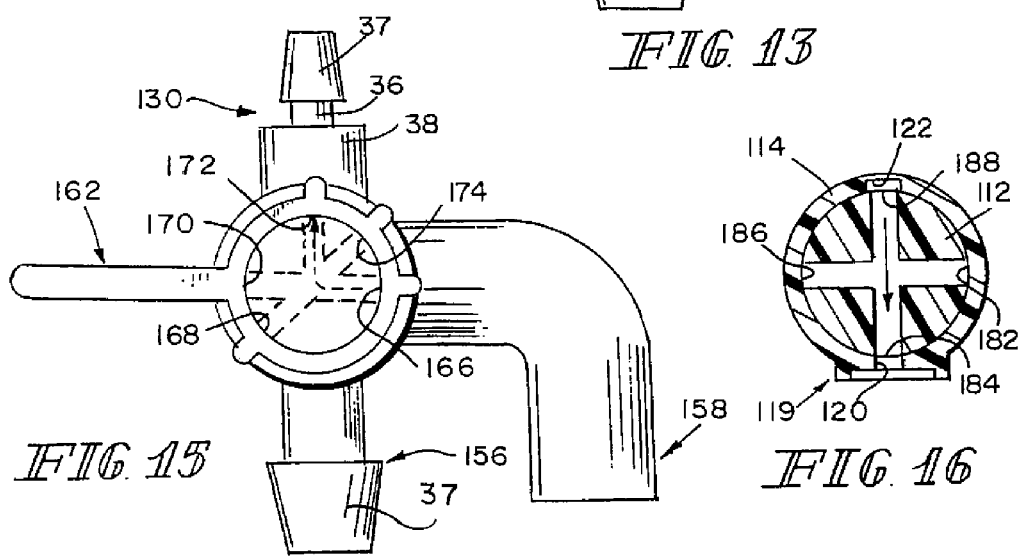

VENTED VACUUM BANDAGE WITH IRRIGATION FOR WOUND HEALING AND METHOD

CROSS-REFERENCE TO RELATED APPLICATIONS

This application is a continuation of U.S. application No. 10/496,623 filed May 25, 2004 now U.S. Pat. No. 7,195,624 which is a US national counterpart application of international Application Ser. No. PCT/US02/41228 filed Dec. 20, 2002, which claims the benefit of U.S. Provisional Application Ser. No. 60/344,588 filed Dec. 26, 2001, U.S. Provisional Application Ser. No. 60/394,809 filed Jul. 10, 2002 and U.S. Provisional Application Ser. No. 60/394,970 filed Jul. 10, 2002, the disclosure of each of which is hereby incorporated by reference herein.

BACKGROUND OF THE INVENTION

The present disclosure relates to vacuum therapy wound treatment systems including a vacuum bandage coupled to a vacuum source and an irrigation source.

The prior art contemplates that chronic wounds may be treated by providing a vacuum in the space above the wound to promote healing. A number of prior art references teach the value of the vacuum bandage or the provision of vacuum in the space above the surface of a chronic wound.

A vacuum bandage is a bandage having a cover for sealing about the outer perimeter of the wound and under which a vacuum is established to act on the wound surface. Applying vacuum to the wound surface promotes healing of chronic wounds. Typically, suction tubes are provided for drawing exudate away from the wound and for creating a vacuum under the cover. The following U.S. Patents establish the nature of vacuum treatment bandages and devices: U.S. Pat. Nos. 6,095,992; 6,080,189; 6,071,304; 5,645,081; 5,636,643; 5,358,494; 5,298,015; 4,969,880; 4,655,754; 4,569,674; 4,382,441; and 4,112,947. All of such references are incorporated herein by reference.

Further, the prior art contemplates that wounds may be treated by providing irrigation in the space above the wound. Typically, a tube is provided in communication with the wound surface of the wound at one end and with an irrigation source an another end. The fluid from the irrigation source travels through the tube to the wound surface.

The prior art further contemplates the use of stopcocks for use in intravenous injections and infusions. Stopcocks may be designed to include multiple ports for directing fluid flow along various paths or channels. The following U.S. Patents establish the nature of stopcocks: U.S. Pat. Nos. 6,158,467; 3,586,049; 2,485,842; 2,842,124; and 6,418,966.

SUMMARY OF THE INVENTION

The present invention comprises one or more of the following features or combinations thereof:

A wound care bandage system is provided for use with a wound. The system, among other things, may be capable of ventilating the wound. The system may include a vacuum source, an irrigation source, a vent in communication with the surrounding atmosphere and with the wound, and a bandage. The vacuum source creates negative pressure above the wound and the irrigation source irrigates the wound. As is herein defined, the term "vent" is or includes any passageway to the atmosphere, unless noted otherwise.

The bandage is configured to lie adjacent the wound to create a sealed environment about the wound. The vent may be positioned between the bandage and the vacuum source. A vacuum passageway of the system may extend between the bandage and the vacuum source, and a vent passageway of the system may extend from the bandage to the vent in communication with the surrounding atmosphere. The vacuum passageway may extend through the vent to the vacuum source.

The system may also include a multi-lumen tube which forms the vacuum passageway and the vent passageway, and a wound dressing member coupled to the multi-lumen tube configured to lie adjacent the wound. The multi-lumen tube may be configured to couple to the vacuum bandage and may include a venting lumen in communication with the surrounding atmosphere and another vacuum/irrigation lumen in communication with either or both of the vacuum source and the irrigation source. Further, the multi-lumen tube may include a vacuum lumen and a separate irrigation lumen distinct from the vacuum lumen.

The system may also include a vent-valve apparatus having the vent or a portion of the vent passageway formed therein. The apparatus provides selective communication between the wound and either the vacuum source or the irrigation source. The apparatus may include a multi-lumen connector configured to communicate with the bandage. The multi-lumen connector may include at least one inner conduit in communication with the vacuum source and/or the irrigation source and at least one outer conduit in communication with the atmosphere. The apparatus may further include a vacuum connector coupled to the vacuum source and an irrigation connector coupled to the irrigation source. An opening of the apparatus may be provided to communicate with the atmosphere and with the outer conduit of the multi-lumen connector.

In one embodiment, the apparatus may include a vent having the multi-lumen connector, and a stopcock coupled to the vent and including the vacuum connector and the irrigation connector. The vent may include a single-lumen connector coupled to the inner conduit of the multi-lumen connector. The vent may further include a housing and a filter housed within the housing. The filter may be in communication with the surrounding atmosphere and with the outer conduit of the multi-lumen connector through the opening.

The stopcock may include a single-lumen connector coupled to the single-lumen connector of the vent and a diverter to selectively couple the single-lumen connector of the stopcock with either the vacuum connector or with the irrigation connector. The stopcock may further include a body and the diverter may be coupled to the body for rotational movement relative to the body. The diverter may include a cut-out portion to selectively communicate the vacuum connector or the irrigation connector with the vent.

In another embodiment, the apparatus may include a body or outer shell defining an aperture and a diverter or inner barrel received within the aperture. The diverter may rotate relative to the outer shell to selectively communicate with the vacuum source or the irrigation source. The outer shell may include the multi-lumen connector, the vacuum connector, and the irrigation connector. The diverter may include a first set of passageways and a second set of passageways formed therethrough. The first set of passageways communicates with the inner conduit of the multi-lumen connector, the vacuum connector, and the irrigation connector. The second set of passageways may communicate with the outer conduit of the multi-lumen connector through a groove or channel formed in the outer shell between the outer conduit and the second set of passageways. The outer shell illustratively includes the opening of the apparatus and the second set of passageways is in selective communication with the opening. A filter may be coupled to the opening.

In yet another embodiment, the apparatus may include a vent and a stopcock coupled to the vent. The vent may include a multi-lumen connector and a first and second single-lumen connector. The stopcock may include a vacuum connector and an irrigation connector. The vacuum connector may include a first portion coupled to the first single-lumen connector of the vent and a second portion coupled to the vacuum source. The irrigation connector may include a first portion coupled to the second single-lumen connector of the vent and a second portion coupled to the irrigation source.

The inner conduit of the multi-lumen connector may be a vacuum conduit and the multi-lumen connector may further include an irrigation conduit. Each of the vacuum and irrigation conduits may be positioned within the outer conduit. The vacuum conduit may be coupled to the first single-lumen connector of the vent and the irrigation conduit may be coupled to the second single-lumen connector of the vent. The vent further may include a housing coupled to the multi-lumen connector and a filter within the housing. The filter may be in communication with the surrounding atmosphere and with the opening through a passageway of the housing.

The stopcock may include a body coupled to the vacuum and irrigation connectors and a diverter received within an aperture of the body. Each of the first and second portions of the vacuum and irrigation connectors may communicate with the aperture of the body. The vacuum connector may illustratively lie in a first horizontal plane and the irrigation connector may illustratively lie in a second horizontal plane.

The diverter may include a first cut-out portion for communication with the vacuum connector and a second cut-out portion for communication with the irrigation connector. The diverter may rotate relative to the body to connect the first and second portions of the vacuum connector with each other and to connect the first and second portions of the irrigation connector with each other to selectively communicate the vacuum source and the irrigation source to the wound.

Other features of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIGS. 1-8 illustrate components of a wound care bandage system of the present disclosure which provides suction, irrigation, and ventilation to a wound;

FIG. 1 is a part perspective, part diagrammatic view of the wound care bandage system located on the leg of a patient and coupled to a vent and to vacuum and irrigation sources through the use of a stopcock or a switch valve;

FIG. 2 is a perspective view of the vent of the system showing a multi-lumen connector for communication with the wound via a multi-lumen tube, a single-lumen connector for communication with the switch valve, and a circular housing holding a filter (in phantom) in communication with the surrounding atmosphere;

FIG. 3 is a side view of the vent, with portions broken away, showing the multi-lumen connector aligned for coupling to the multi-lumen tube, the single-lumen connector aligned for coupling to a single lumen tube, a passageway of the vent extending between outer lumens of the multi-lumen tube and the filter of the vent, and further showing a thin, flexible wound dressing member of the bandage coupled to the multi-lumen tube by a barbed coupler;

FIG. 4 is a sectional view of the multi-lumen tube taken along line 4-4 of FIG. 3 showing an inner lumen of the tube for communication with the vacuum source and the irrigation source of the system and four outer lumens of the tube for communication with the filter and surrounding atmosphere to aspirate an area above the wound;

FIG. 5 is an exploded perspective view of the switch valve and vent of the system showing a vent connector of the valve aligned for coupling to the single-lumen connector of the vent, a vacuum connector for communication with the vacuum source, an irrigation connector for communication with the irrigation source, and a handle or diverter for providing selective communication between the vent connector and either the vacuum source or the irrigation source;

FIGS. 6a and 6b are perspective views of the handle of the switch valve showing a grip and a stem of the handle and further showing a cut-out portion of the stem for selective communication between the vent, vacuum, and irrigation connectors of the switch valve;

FIG. 7 is a sectional view taken along line 7-7 of FIG. 5 showing the handle of the switch valve in an irrigation position so that the cut-out portion provides a passageway between the irrigation connector and the vent connector to permit fluid from the irrigation source to run through the switch valve to the wound;

FIG. 8 is a sectional view similar to FIG. 7 showing the handle of the switch valve in a vacuum position so that the cut-out portion provides a passageway between the vacuum connector and the vent connector to permit the vacuum source to draw fluid and exudate from the wound;

FIGS. 9-16 illustrate components of another wound care bandage system in accordance with the present disclosure which also provides suction, irrigation, and ventilation to the wound;

FIG. 9 is a part perspective, part diagrammatic view similar to FIG. 1 showing the wound care bandage system of FIGS. 9-16 including a two-level stopcock or switch valve in selective communication with the bandage, vacuum source, and irrigation source of the system, and further showing the two-level stopcock including a vent coupled to a filter;

FIG. 10 is an exploded view of the two-level stopcock showing an inner barrel or handle and an outer shell, with portions broken away, and further showing the inner barrel having a grip and a stem including an upper level of ports for communication with either the vacuum source or the irrigation source, depending on the position of the inner barrel relative to the outer shell, and a lower level of ports for communication with the vent, and further showing an inner vent groove of the outer shell for providing communication between the outer lumens of the multi-lumen tube and the lower level ports of the barrel;

FIGS. 11-16 show three positions of the two-level stopcock provided by moving the inner barrel relative to the outer shell to selectively align certain upper level ports of the inner barrel with the vacuum and irrigation connectors of the outer shell and to selectively align certain lower level ports with the vent of the outer shell;

FIGS. 11 and 12 show the two-level stopcock in a vented vacuum position so that the vacuum source and vent are in communication with the wound to create a negative pressure adjacent the wound while drawing air into the system through the vent and over the wound to aspirate the passageways of the system;

FIG. 11 is a top view of the two-level stopcock in the vented vacuum position showing a passageway (in phantom) connecting the vacuum connector and the multi-lumen tube connector;

FIG. 12 is a sectional view taken along line 13-13 of FIG. 9 when the two-level stopcock is in the vented vacuum position showing venting passageways of the inner barrel and showing one passageway connecting the vent groove of the outer shell with the vent;

FIGS. 13 and 14 show the two-level stopcock in a vacuum position where only the vacuum source is in communication with the wound to create a negative pressure adjacent the wound;

FIG. 13 is a top view similar to FIG. 11 of the stopcock in the vacuum position after the handle has been turned clockwise from the vented vacuum position shown in FIG. 11, and showing a passageway (in phantom) between the vacuum connector and the multi-lumen tube connector;

FIG. 14 is a sectional view similar to FIG. 12 showing the two-level stopcock in the vacuum position where none of the venting passageways of the inner barrel connect the vent groove of the outer shell with the vent;

FIGS. 15 and 16 show the two-level stopcock in a vented irrigation position where the irrigation source and the vent are in communication with the wound;

FIG. 15 is a top view similar to FIGS. 11 and 13 showing the two-level stopcock in the vented irrigation position after the handle has been turned clockwise from the vacuum position shown in FIG. 13, and showing a passageway (in phantom) between the irrigation connector and the multi-lumen connector;

FIG. 16 is a sectional view similar to FIGS. 12 and 14 showing the two-level stopcock in the vented irrigation position and showing a passageway of the inner barrel connecting the vent groove of the outer shell with the vent;

FIG. 17 is a part perspective, part diagrammatic view of the multi-lumen tube coupler in use with the system shown in FIGS. 9-16;

FIG. 18 is a perspective view of the multi-lumen tube coupler showing an inner passageway for communication with each inner lumen of the multi-lumen tubes and an outer passageway for communication with each outer lumen of the multi-lumen tubes, and also showing a contoured upper surface and a flat bottom surface of the tube coupler;

FIG. 19 is a sectional view of the multi-lumen tube coupler coupled to two multi-lumen tubes showing a flow path of fluids through the multi-lumen tubes and the coupler;

FIG. 20 is a part perspective, part diagrammatic view similar to FIG. 1 showing the wound care bandage system of FIGS. 20-28 including a vent coupled to the bandage via a multi-lumen tube (shown in FIG. 21) and a stopcock or switch valve coupled to the vent (via two single-lumen tubes) to provide selective communication between the bandage and the irrigation and vacuum sources;

FIG. 21 is an end view of the multi-lumen tube of the system shown in FIGS. 20-28 showing the tube including a vacuum lumen, an irrigation lumen, and four outer vent lumens formed within a body of the tube;

FIG. 22 is a perspective view of a "Y-connecter" of the system shown in FIGS. 20-28 for coupling the wound dressing member of the bandage with the multi-lumen tube shown in FIG. 21 showing a bandage portion of the connector for insertion within a connector of the member, a vacuum portion for insertion within the vacuum lumen of the multi-lumen tube, and an irrigation portion for insertion within the irrigation lumen of the multi-lumen tube;

FIG. 23 is a perspective view of the vent of the system shown in FIG. 20 showing a multi-lumen connector for coupling with the multi-lumen tube of FIG. 21, a vacuum connector for communication with the vacuum source via a single-lumen tube, an irrigation connector for communication with the irrigation source via a separate single-lumen tube, and also showing a filter housing coupled to the multi-lumen connector for communication with the venting lumens of the multi-lumen tube and with the atmosphere;

FIG. 24 is a sectional view of the vent coupled to the multi-lumen tube and the two single-lumen tubes showing a filter of the vent (in phantom), the separate vacuum, irrigation, and vent passageways formed through the vent, and also showing the Y-connecter of the system coupled to the multi-lumen tube and to the member;

FIG. 25 is an exploded perspective view of the stopcock or switch valve of the system shown in FIGS. 20-28 showing two separate passageways through a body of the stopcock for separate communication with the vacuum source and the irrigation source, and showing a handle or diverter, having two cut-out portions, to be received within the body of the stopcock;

FIGS. 26-28 are sectional views showing the stopcock in an irrigation position, a vacuum position, and an off position;

FIG. 26 is a sectional view of the stopcock showing the stopcock in the vacuum position so that a first cut-out portion of the handle creates a passageway between first and second portions of a vacuum conduit of the stopcock;

FIG. 27 is a sectional view similar to FIG. 26 showing the stopcock in the irrigation position where the handle has been rotated in a clockwise direction from that shown in FIG. 26 so that a second cut-out portion (shown in phantom) connects first and second portions of an irrigation conduit with each other;

FIG. 28 is a sectional view similar to FIGS. 26 and 27 showing the stopcock in the off position where the handle has been rotated 180 degrees from that shown in FIG. 27 so that neither the first nor the second cut-out portions connect the first and second portions of either of the vacuum conduit or the irrigation conduit;

FIG. 29 is a part perspective and part diagrammatic view of a vacuum bandage system of the present disclosure showing a wound dressing member of the bandage including a cover having a port and a wound contacting layer having a wound contacting surface and channels formed in an opposite surface to cooperate with the cover and form passageways of the member in communication with the port and a vacuum source and/or an irrigation source, and also showing a vent line or tube having a first end for communication with the passageways and a second end in communication with the surrounding atmosphere through a filter and a cap;

FIG. 30 is a sectional view of the bandage of FIG. 29 positioned within a wound and showing a sealing film of the bandage providing a sealed vacuum space above the wound, the first end of the vent line in communication with the vacuum space, and the second end of the vent line coupled to the filter and to the cap outside of the vacuum space;

FIG. 31 is a sectional view taken along line 31-31 of FIG. 30 showing the vent line and a vacuum tube coupled to each other by a coupler;

DETAILED DESCRIPTION OF THE DRAWINGS

Figure 9:
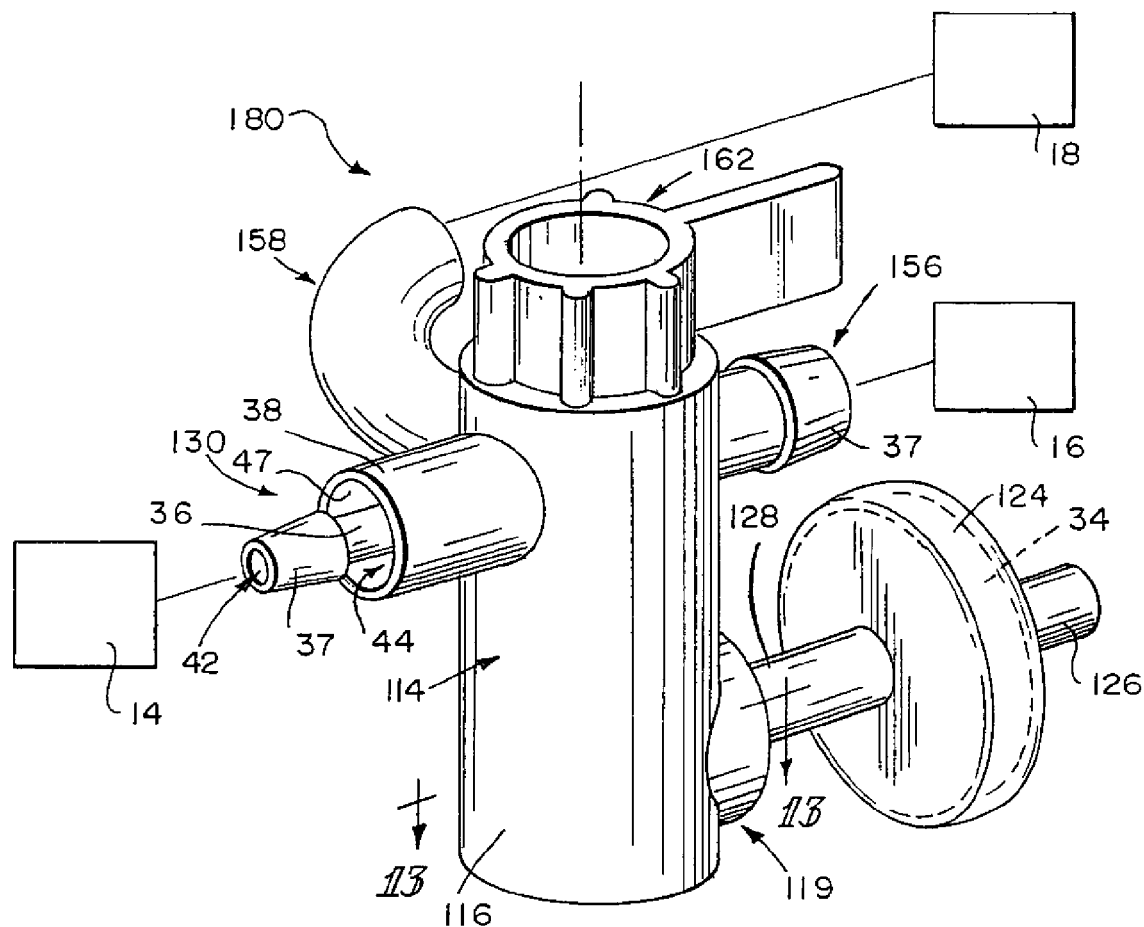

A wound care bandage system is provided which has the capability to create negative pressure adjacent the wound, to irrigate the wound, and to ventilate the wound. A vent of the system is provided to communicate with the wound and with the surrounding atmosphere. In some embodiments, a vent-valve apparatus or a vent and valve combination of the system is in communication with the wound and with a vacuum source and an irrigation source of the wound. The vent-valve apparatus includes the vent which is in communication with the surrounding atmosphere and a diverter to provide selective communication between the wound and the irrigation source or between the wound and the vacuum source, as is described in greater detail below.

One embodiment of a wound care bandage system 10 is shown in FIGS. 1-8 and is provided to allow a caregiver to create a negative pressure above a wound surface (not shown) of a wound 200 (see FIG. 20) through the use of an illustrative vacuum bandage 14 and a vacuum source 16, as shown in FIG. 1. System 10 further allows a caregiver to irrigate the wound surface through the use of an irrigation source 18. Additionally, system 10 ventilates the wound during the application of negative pressure to the wound and irrigation of the wound through use of a vent 19 in communication with the surrounding atmosphere.

The system 10 further includes a stopcock or switch valve 50 coupled to vent 19. Switch valve 50 allows a caregiver to selectively provide communication between the wound and either vacuum source 16 or irrigation source 18. As is herein defined, the terms switch valve and stopcock are used interchangeably to describe an apparatus for selectively controlling and/or diverting fluid flow therethrough. As shown in FIG. 1, switch valve 50 is coupled to vent 19 via a single-lumen tube 52. However, switch valve 50 may also be coupled directly to vent 19, as shown in FIG. 5 and described in more detail below. The vent 19 and switch valve 50 (and tube 52, if used) cooperate to create a vent-valve assembly 80 to allow a caregiver to toggle between different modes such as vented vacuum therapy and vented irrigation therapy. The system 10 incorporates two separate fluid lines. One fluid line selectively provides vacuum suction or irrigation to the wound while the other fluid line vents the system 10 by providing communication between the wound and the surrounding atmosphere to create air flow above the wound.

Vacuum bandage 14, as shown in FIG. 1, is provided for use with the wound and is sealed about the wound by a cover or sealing film 13 of bandage 14 to create a sealed environment between the wound and sealing film 13 in which a negative pressure can be established. Bandage 14 is selectively coupled to both vacuum source 16 and irrigation source 18 through the use of switch valve 50, as is described in more detail below.

Bandage 14 promotes the healing of the wound by providing vacuum therapy to the wound to promote blood flow and remove exudate from the wound surface and by providing for irrigation of the wound with fluids such as saline, for example. An illustrative wound treatment apparatus having a wound temperature control system, a medicine delivery system, and a drainage system is disclosed in U.S. Pat. No. 6,458,109. An illustrative vacuum and irrigation system is disclosed in U.S. Patent Publication No. US 2002/0161317 A1. Additionally, an illustrative vacuum bandage is disclosed in U.S. Patent Publication No. US 2002/0065494 A1. Alternative vacuum bandages are disclosed in U.S. Patent Publication No. US 2002/0082567 A1. Further, a vacuum bandage system including a controller of the system is disclosed in U.S. Patent Publication No. US 2002/0198504 A1 and in U.S. Patent Publication No. US 2002/0198503 A1. All of these applications are hereby incorporated herein by reference.

As mentioned above, system 10 incorporates two separate fluid lines to provide vented vacuum therapy and vented irrigation therapy to the wound. Venting of bandage 14 is disclosed in U.S. Patent Application Ser. No. 60/344,588 filed on Dec. 26, 2001. This application is hereby incorporated herein by reference. Venting provides for increased air flow through bandage 14 and above or adjacent the wound while vacuum source 16 applies suction to the wound. System 10 is also vented while irrigation source 18 provides fluid to the wound. Without providing for ventilation of the system 10 during operation of vacuum source 16, a generally closed system is created between vacuum bandage 14 and vacuum source 16. For example, in bandages without a ventilation system, once the requisite amount of air has been removed by the vacuum source 16 to create a predetermined negative pressure at the wound surface, it is possible for the system to become generally static, inhibiting much, if any, fluid flow from the wound surface. In some embodiments disclosed herein, static conditions may be created at the wound surface.

Ventilation of the system 10, while drawing a negative pressure over the wound, acts to prevent the system 10 from becoming static by drawing air in from the surrounding atmosphere through vent 19, to bandage 14 to create air flow above the wound, and out through a vacuum tube in communication with vacuum source 14. Therefore, venting the system 10 increases air flow above the wound while vacuum source 16 applies suction to the wound.

The two fluid lines for ventilation and vacuum/irrigation of the wound are provided in multi-lumen tube 20, shown in cross-section in FIG. 4. As shown in FIG. 3, tube 20 is coupled to a connector 15 of bandage 14, and is therefore in communication with the wound at one end 21 and is coupled to vent 19 at the other end 23. Tube 20 includes an inner lumen 22 for selective communication with the vacuum source 16 and the irrigation source 18 and outer lumens 24 formed in a body or outer wall 25 of tube 20 for communication with the surrounding atmosphere through vent 19. Inner lumen 22 thus defines a portion of a vacuum/irrigation passageway 42 and outer lumens 24 each define a portion of a ventilation passageway 44.

As shown in FIG. 4, tube 20 includes four outer lumens 24 spaced about inner lumen 22. It is within the scope of this disclosure, however, to include a multi-lumen tube having one or more outer lumens in communication with the surrounding atmosphere and one or more inner lumens in selective communication with the vacuum source 16 and the irrigation source 18. Illustratively, the outer diameter 26 of tube 20 is 0.250 inch (6.300 mm), the inner diameter 28 of tube 20 (the diameter of inner lumen 22) is 0.125 inch (3.150 mm), and the diameter 29 of each outer or peripheral lumen is 0.014 inch (0.353 mm). Although tube 20 includes the above dimensions, it is within the scope of this disclosure to provide any suitable multi-lumen tube having lumens of any suitable size.

As shown in FIG. 3, bandage 14 illustratively includes a thin, flexible wound dressing member 12 having connector 15 coupled to tube 20 by a barbed tube coupler 11. Member 12 lies adjacent to and generally conforms to the wound surface. Sealing film 13 is placed over member 12 and sealed around tube 20 to the patient's healthy skin 27 surrounding the wound, as shown in FIG. 1. Illustratively, connector 15 is in communication with the wound by a plurality of passageways 66 of member 12 and a plurality of holes 67, each in communication with one of the passageways 66, formed in a bottom surface 68 of member 19. Tube coupler 11 connects inner lumen 22 of tube 20 with connector 15. Each outer lumen 24 is open at an end 21 of tube 20. This allows air to be drawn in from the atmosphere through vent 19, to flow through outer lumens 24 and exit tube 20 at end 21, to circulate around member 12 to the wound surface, and to flow through the holes 67 and passageways 66 of member 12 into a vacuum/irrigation passageway 42 formed in part by lumen 22. The negative pressure created by vacuum source 16 causes air to flow through system 10 in this manner.

Although bandage 14 is described above, it is within the scope of this disclosure for the system 10, and other alternative systems described below, to include any suitable bandage or wound dressing member coupled to the vacuum source 16 to communicate negative pressure from the vacuum source 16 to the wound. Bandage 14, therefore, is merely an illustrative bandage of the wound care bandage systems disclosed herein.

As mentioned above, system 10 further includes vent 19. Vent 19 is coupled to end 23 of tube 20, as shown in FIG. 1, and is illustratively shown to be coupled to patient's healthy skin 27 by tape 94, for example. As shown in FIGS. 2 and 3, vent 19 includes a multi-lumen or wound connector 30 for coupling with multi-lumen tube 20 and a single-lumen connector 32 for coupling with single-lumen tube 52 or for coupling directly to switch valve 50, as shown in FIG. 5. Vent 19 further includes a filter 34, shown in phantom in FIGS. 2 and 3, housed within a filter housing 40. Multi-lumen connector 30 includes an inner conduit 36 and an outer conduit 38 concentric and coaxial with inner conduit 36 along an axis 39, as shown in FIG. 3. An edge 41 of inner conduit 36 is substantially coplanar with an edge 43 of outer conduit 38. An annular space 45 is defined between a cylindrical inner surface 47 of outer conduit 38 and a cylindrical outer surface 53 of inner conduit 36.

Inner conduit 36 is in communication with vacuum source 16 and irrigation source 18 through stopcock 50 and defines a portion of the vacuum/irrigation passageway 42. The vacuum/irrigation passageway 42 extends through inner lumen 22, a portion of vent 19 and stopcock 50. Outer conduit 38, or annular space 45, is in communication with the surrounding atmosphere and defines a portion of vent passageway 44. The vent passageway 44 extends through outer lumens 24 and a portion of vent 19 to the surrounding atmosphere.

As shown in FIG. 3, a ridge or stop 59 is coupled to inner surface 47 of outer conduit 38 to prevent tube 20 from being inserted too far within connector 30 and thus sealing off outer lumens 24. Stop 59 prevents vent passageway 44 from becoming closed off and keeps vent passageway 44 open to receive air from the surrounding atmosphere. Vent 19 includes three evenly spaced stops 59 coupled to inner surface 47. It is within the scope of this disclosure, however, to include a vent having any number of stops 59 or the like to prevent vent passageway 44 from becoming closed off.

When connecting multi-lumen tube 20 with vent 19, inner conduit 36 is received within inner lumen 22 of tube 20. Wall 25 of tube 20, which includes outer lumens 24, is received within annular space 45 of connecter 30. Tube 20 is, therefore, press fit into connector 30 and, if desired, may be permanently coupled to connecter 30 through the use of adhesives applied to the appropriate surfaces of connecter 30 and/or tube 20.

Connector 32 is received within single-lumen tube 52 when connecting vent 19 to tube 52. Tube 52 is press fit onto connector 32 so that an end 65 of single-lumen tube 52 abuts an annular shoulder surface 69 of conduit 30. As noted above, vent 19 may also be coupled directly to switch valve 50 through the use of a luer lock connection shown in FIG. 5 and discussed further below.

As shown in FIG. 3, vent 19 includes an opening or passageway 46 leading between outer conduit 38 and filter 34 to connect annular space 45 with the surrounding atmosphere. Opening 46 extends radially away from conduit 30 and is generally perpendicular to axis 39. Opening 46 is defined by cylindrical wall 27. Illustratively, opening 46 has a diameter of 0.100 inch (2.54 mm), however, it is within the scope of this disclosure to include a vent having any suitably sized opening for receiving air from the surrounding atmosphere.

Further illustratively, filter 34, is a 0.2 micron anti-microbial filter for preventing bacteria and other microorganisms in the atmosphere from entering the vent 19 and traveling along vent passageway 44 below sealing film 13 of bandage 14 to the wound. Such an air filter, for example, is made by W.L. Gore & Associates, Inc. of Elkton, Md. As mentioned above, filter 34 is housed within housing 40. Housing 40 has a circular top wall 31, a cylindrical sidewall 33, and a circular bottom wall (not shown). Filter 34 is a generally circular dish of material sandwiched between top wall 31 and the bottom wall. The bottom wall has apertures, openings, or the like so that filter 34 is in communication with the surrounding atmosphere. Further, the bottom wall is removable so that filter 34 may be replaced if needed. Vent 19 further includes reinforcement ribs 35 appended to top wall 31 of housing 40 and wall 27 defining passageway 46.

In operation, vent 19 is used during both vacuum and irrigation modes of the system. As mentioned before, vent 19 provides increased air flow through bandage 14 and above the wound. Vent 19 also creates an open system and prevents the system from becoming static. The air flow path while vacuuming the system begins as air is drawn in from the surrounding atmosphere into filter housing 40 of vent 19 and through filter 34. The air then travels through opening 46 into annular space 45 defined by outer conduit 38 and through outer lumens 24 of multi-lumen tube 20. The air travels through the outer lumens 24 from vent end 23 of tube 20 to end 21 of tube 20, a portion of which is positioned under sealing film 13, to communicate with the wound. Vacuum source 16 then draws the air around wound dressing member 12 through passageways 66 at an open peripheral edge of member 12 and through holes 67 into passageways 66. Air is then drawn from passageways 66 into connector 15 of member 12, through barb 11, and through inner lumen 22 of multi-lumen tube 20 toward vacuum source 14.

It is also within the scope of the disclosure for the caregiver to close off vent 19 while vacuuming or irrigating the wound. Vent 19 may be closed in a number of ways. For example, a cap or valve (not shown) may be coupled to filter 34 or filter housing 40 to prevent air flow through filter 40. It is within the scope of this disclosure to include a vent having other suitable means of preventing air flow therethrough.

As shown in FIG. 3 and mentioned above, inner conduit 36 and outer conduit 38 form separate passageways through vent 19. Inner conduit 36 is in communication with and forms a portion of vacuum/irrigation passageway 42 which extends through inner lumen 22, a portion of vent 19 and on to switch valve 50. Outer conduit 38 is in communication with and forms a portion of vent passageway 44, which extends through outer lumens 24 and a portion of vent 19. Vent passageway 44 is in communication with the atmosphere through filter 34.

As shown in FIG. 1, system 10 further includes switch valve 50. Switch valve 50 is positioned between vent 19 and vacuum and irrigation sources 16, 18. Single-lumen tube 52 is coupled to and extends between single-lumen connector 32 of vent 19 and switch valve 50 and forms a portion of vacuum/irrigation passageway 42. Switch valve 50, includes a vent connector 54 which can be coupled either to single-lumen tube 52, as shown in FIG. 1, or directly to connecter 32 of vent 19, as shown in FIG. 5, through the use of a luer lock. Single-lumen connector 32 includes a female thread portion 55 of the luer lock, and vent connector 54 of switch valve 50 includes a male portion 57 of the luer lock so that the two can be coupled together.

As shown in FIG. 5, switch valve 50 includes a body 60 and a handle or diverter 51 coupled to body 60. Body 60 includes vent connector 54, a vacuum connector 56 in communication with vacuum source 16, and an irrigation connector 58 in communication with irrigation source 18. Vent connector 54 forms another portion of vacuum/irrigation passageway 42 and is in selective communication with vacuum source 16 and irrigation source 18. Vacuum/irrigation passageway 42 therefore extends from end 21 of inner lumen 22 of multi-lumen tube 20 to multi-lumen connector 30 of vent 19, through inner conduit 36 of vent 19, out connector 32 of vent 19, to vent connector 54 of switch valve 50 and partially through switch valve 50 to diverter 51 of switch valve 50.

Switch valve 50 includes diverter 51 for selectively providing communication between vacuum source 16 and bandage 14 and between irrigation source 18 and bandage 14. Diverter 51 includes a grip 62 and a stem 64 coupled to grip 62, as show in FIGS. 6a and 6b. Diverter 51 is rotatably movable relative to body 60 to selectively provide communication between either vent connector 54 and irrigation connector 58 or between vent connector 54 and vacuum connector 56. A caregiver rotates diverter 51 between an irrigation position shown in FIG. 7 and a vacuum position shown in FIG. 8 depending on whether the wound is to receive vacuum or irrigation treatment, respectively. Switch valve 50 allows the caregiver to easily switch between communication with vacuum source 16 and irrigation source 18 without the need to disconnect or reconnect various tubes from each of the vacuum source 16 and/or irrigation source 18, for example.

As shown in FIGS. 7 and 8, body 60 includes an aperture 61 for receiving stern 64 of diverter 51. Vent connector 54, vacuum connector 56, and irrigation connector 58 each form a respective opening 82, 84, 86 in communication with aperture 61. As diverter 51 is rotated, a cut-out portion 63 of stem 64 provides a passageway between vent connector 54 and vacuum connector 56 when diverter 51 is in the vacuum position, for example. When diverter 51 is in the irrigation position, cut-out portion 63 provides a passageway between vent connector 54 and irrigation connector 58. Diverter 51 is also movable to an off position where cut-out portion 63 does not provide any communication between the connectors 54, 56, 58.

In addition to vacuum/irrigation passageway 42 and vent passageway 44, system 10 further includes a separate vacuum passageway 70 and a separate irrigation passageway 72. Vacuum connector 56 defines a portion of vacuum passageway 70 and irrigation connector 58 defines a portion of irrigation passageway 72. As shown in FIG. 1, vacuum connector 56 is coupled to a vacuum tube 74 which is, in turn, coupled to vacuum source 16. The vacuum passageway 70, therefore, extends from opening 84 of body 60 through vacuum connector 56 and vacuum tube 74 to vacuum source 16.

As shown in FIG. 1, irrigation connector 58 is coupled to an irrigation tube 76 which is, in turn, coupled to irrigation source 18. The irrigation passageway 72, therefore, extends from opening 86 of body 60 through irrigation connector 58 and irrigation tube 76 to irrigation source 18. Thus, at opening 82 of body 60, vacuum/irrigation passageway 42 ends and is split into separate vacuum and irrigation passageways 70, 72.

As shown in FIG. 5, an attachment 88 is coupled to irrigation connector 58. Attachment 88 includes a first inlet 90 for communication with irrigation tube 76 and irrigation source 18 and a second inlet 92 for communication with a hand-held syringe (not shown). Attachment 88 provides two means of introducing fluids into system 10. Second inlet 92 allows a caregiver to manually introduce fluids into system 10 while irrigation source 18 includes automatic controls for introducing fluids into system 10 through first inlet 90. A slot 96 of irrigation connector 58 receives a portion of second inlet 92 to secure attachment 88 within irrigation connector 58.

As mentioned above, system 10 allows a caregiver to treat the wound using vented vacuum therapy through the use of vent 19 with vacuum source 16 and using vented irrigation therapy through the use of irrigation source 18 and vent 19. To provide vented vacuum therapy to the wound, the caregiver moves diverter 51 to the vacuum position, shown in FIG. 8, so that cut-out portion 63 of stem 64 connects opening 82 of vent connector 54 with opening 84 of vacuum connector 56. Therefore, irrigation connector 58 and irrigation passageway 72 are closed off and vacuum/irrigation passageway 42 is connected with vacuum connector 56 and vacuum passageway 70. Vent passageway 44 is kept open to the surrounding atmosphere. The negative pressure provided by vacuum source 16 above wound 12 acts to draw air in from the atmosphere through filter 34 of vent 19 and outer lumens 24. As mentioned above, vent 19 is provided to aspirate the system 10 by creating an air flow path from the atmosphere to the bandage 14, over the wound, and out through inner lumen 22 in communication with vacuum source 16.

To create vented irrigation of wound 12, a caregiver moves diverter 51 to the irrigation position so that cut-out portion 63 of stem 64 connects opening 82 of vent connector 54 with opening 56 of irrigation connector 58. Therefore, irrigation passageway 72 of the irrigation connector 58 is in communication with the vacuum/irrigation passageway 42 of the vent connector 54. The vacuum passageway 70 is thus cut off from communication with the vacuum/irrigation passageway 42. Irrigation fluid is then dispensed from irrigation source 18 through irrigation passageway 72 of tube 76 and switch valve 50 to the vacuum/irrigation passageway 42 through vent connector 54, tube 52, vent 19, and inner lumen 22 of multi-lumen tube 20 to wound 12. Vent 19 is left in an open position to allow air to flow out of bandage 14 while fluid from irrigation source 18 is channeled to the wound. As mentioned above, it is also within the scope of this disclosure to provide non-vented irrigation of the wound by closing off vent 19 from the surrounding atmosphere while providing fluid to the wound through irrigation source 18.

As mentioned above, the combination of vent 19, and switch valve 50 is defined as vent-valve assembly 80. If desired, assembly 80 may also include tube 52 or another conduit or passageway between vent 19 and switch valve 50. Assembly 80 provides a caregiver with the ability to toggle or selectively switch between the vented vacuum mode of therapy and the vented irrigation mode of therapy for the treatment of the wound. As mentioned above, it is within the scope of this disclosure to include a vent which is able to be closed off from communication with the surrounding atmosphere so that vacuum only and/or irrigation only therapy may be provided as well.

An alternative vent-valve assembly 180 is provided for use with system 10, as shown in FIGS. 9-16. Assembly 180 includes a stopcock or valve portion in selective communication with vacuum source 16 and irrigation source 18 and a vent portion in communication with the surrounding atmosphere. Assembly 180 is configured to selectively provide three modes of therapy: vacuum therapy, vented vacuum therapy, and vented irrigation therapy.

As shown in FIG. 9, vent-valve assembly 180 is positioned between illustrative bandage 14 of system 10 and vacuum and irrigation sources 16, 18. Assembly 180 serves a similar function as assembly 80, including vent 19 and stopcock 50, shown in FIGS. 1-8. Similar to assembly 80, assembly 180 is in communication with bandage 14, vacuum source 16, and irrigation source 18 of system 10. Assembly 180 is operated by a caregiver during the treatment of a patient to change from mode to mode as desired.

Figure 10:
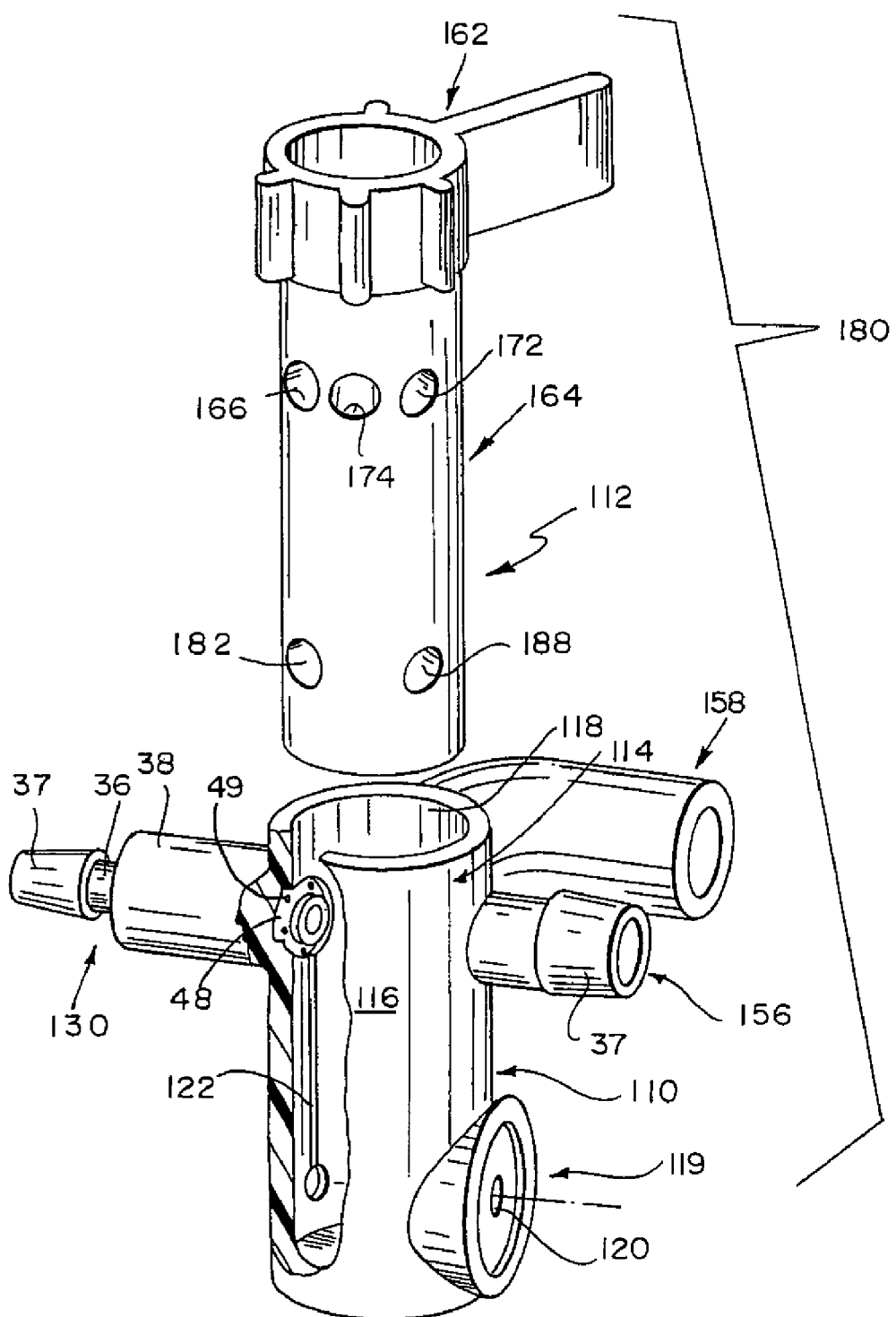

As shown in FIG. 10, assembly 180 includes an outer shell or body 110 and a diverter or inner barrel 112. Inner barrel 112 is normally positioned within outer shell 110, as shown in FIG. 9, and is rotatable relative to outer shell 110 between three different positions which correlate with the three available modes: vacuum, vented vacuum, vented irrigation. Outer shell 110 includes a cylindrical hub 114 having an outer surface 116 and in inner surface 118, shown in FIG. 10. Outer shell 110 further includes a multi-lumen or wound connector 130, a vent 119, a vacuum connector 156, and an irrigation connector 158. Suitable coupling means such as a C-clip (not shown) to fit around inner barrel 112, a pin (not shown) through outer shell 110 and inner barrel 112, for example, are provided to prevent inner barrel or diverter 112 from being inadvertently separated from body 110. Such coupling means are also provided for use with stopcocks 50 and 250 (discussed below) to prevent the handle of each from being inadvertently decoupled from the body of each.

Similar to multi-lumen connector 30 of vent 19, multi-lumen connector 130 of assembly 180 includes inner conduit 36 and outer conduit 38 spaced apart from and concentric with inner conduit 36. Inner conduit 36 defines a portion of vacuum/irrigation passageway 42 and outer conduit 38 defines a portion of vent passageway 44 of system 10. Inner conduit 36 is received within inner lumen 22 of tube 20. Wall 25 of tube 20, which includes outer lumens 24, is received within outer conduit 38 of multi-lumen connector 130. As shown in FIG. 9, inner conduit 36 is coupled to a barb 37. Barb 37 is received within inner lumen 22 as well and helps maintain the connection between tube 20 and multi-lumen connector 130. It is within the scope of this disclosure for multi-lumen connector 30 of vent 19 to have barb 37 formed integrally with inner conduit 36.

As shown in FIG. 10, outer conduit 38 includes a partition 48 having multiple vent holes 49 formed therethrough. Air traveling through lumens 24 also travels through the holes 49 to a vent groove 122 formed in inner surface 118 of hub 114. It is not necessary for outer lumens 24 of tube 20 to align directly with one of the vent holes 49. A stop (not shown), similar to stop 59, is coupled to inner surface 47 of outer conduit 38 to prevent tube 20 from being inserted too far within connecter 130. Vent groove 122 connects outer conduit 38 with vent 119, as is described in more detail below.

Figure 17:
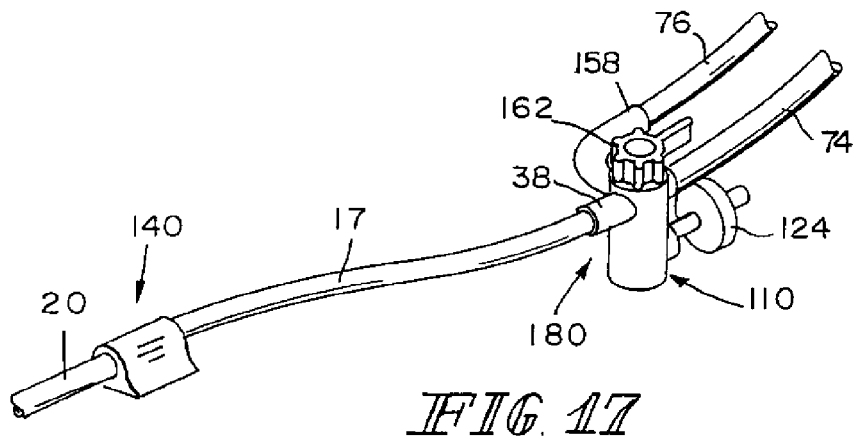
FIGS. 17-19 show a multi-lumen tube coupler according to the present disclosure for use with either of the systems illustrated in FIGS. 1-8 and FIGS. 9-16 described above for coupling two multi-lumen tubes together.

Vacuum connector 156 communicates with vacuum source 16 through vacuum tube 74. Vacuum connector 156 includes barb 37 received within tube 74. Vacuum connector 156 and vacuum tube 74 form vacuum passageway 70 of system 10. Irrigation connector 158 communicates with irrigation source 18 through irrigation tube 76, as shown in FIG. 17. Irrigation connector 158 and irrigation tube 76 form the irrigation passageway 72 of system 10. Vacuum connector 156 and irrigation connector 158 are each in selective communication with multi-lumen connector 130, as is described below. As shown in FIG. 9, air filter 34, contained within a housing 124, is coupled to vent 119 and is received within an aperture 120 (shown in FIG. 10) of vent 119. Housing 124 includes an air inlet tube 126 and a connector tube 128 coupled to vent 119 and in communication with aperture 120 of vent 119.

Diverter 112, as shown in FIG. 10, includes a grip 162 and a cylinder or stem 164 coupled to grip 162. Cylinder 164 includes an upper level of holes and a lower level of holes, as shown in FIG. 10. As shown in phantom in FIGS. 11, 13, and 15, the upper level of holes includes first, second, third, fourth, and fifth holes 166, 168, 170, 172, 174, respectively. As shown in FIGS. 12, 14, and 16, the lower level of holes includes first, second, third, and fourth holes 182, 184, 186, and 188, respectively. The upper level of holes communicate with inner conduit 36 of multi-lumen connector 130 and with each of the vacuum and irrigation connectors 156, 158. The lower level of holes communicate with outer conduit 38 and aperture 120 of vent 119. The upper holes of cylinder 164 form interconnecting passageways through cylinder 164 to selectively connect inner conduit 36 with vacuum conduit 156 and irrigation conduit 158 and the lower holes form passageways through cylinder 164 to selectively connect outer conduit 38 with vent 119, as is described in more detail below.

As shown in FIGS. 11 and 12, assembly 180 is in the vented vacuum position. As shown in FIG. 11, the upper holes are positioned so that hole 166 is in communication with inner conduit 36 and hole 170 is in communication with vacuum connector 156 to provide a passageway between inner conduit 36 and vacuum connector 156. The other holes 168, 172 and 174 are not in communication with any of the connectors 130, 156, 158 of outer shell 110. Looking now to the lower level of holes shown in FIG. 12, hole 182 is in communication with vent groove 122 and hole 186 is in communication with aperture 120 of vent 119 to provide a passageway between vent groove 122 and vent 119 so that outer lumens 24 of tube 20 are in communication with the surrounding atmosphere.

By rotating grip 162 clockwise (as viewed from the top of apparatus 180), a caregiver rotates inner barrel 112 relative to outer shell 110 to move assembly 180 to the vacuum position shown in FIGS. 13 and 14. In the vacuum position, upper level hole 174 is in communication with inner conduit 36 of multi-lumen connector 130 and hole 168 is in communication with vacuum connector 156 to provide a passageway between inner conduit 36 and vacuum connector 156. In the vacuum position, however, vent passageway 44 of system 10 is prevented from communicating with the surrounding atmosphere through vent 119. As shown in FIG. 14, for example, none of the lower level holes are in communication with either vent groove 122 or aperture 120 of vent 119.

By rotating grip 162 still further clockwise, a caregiver rotates inner barrel 112 relative to outer shell 110 to move assembly 180 to the vented irrigation position shown in FIGS. 15 and 16. FIG. 15 shows the orientation of the upper level holes of the inner barrel 112 while assembly 180 is in the vented irrigation position. Hole 172 is in communication with inner conduit 36 of multi-lumen connector 130 and hole 166 is in communication with irrigation connector 158 to provide communication between inner conduit 36 and irrigation connector 158. FIG. 16 shows the orientation of the lower level holes when stopcock 180 is in the vented irrigation position. Hole 188 is in communication with vent groove 122 and hole 184 is in communication with aperture 120 of vent 119 so that outer conduit 38 is in communication with vent 119 to allow air from the surrounding atmosphere to enter system 10. It is also within the scope of this disclosure for assembly 180 to be in an "off" position where none of the upper level passageways connect any of the connecters 130, 158, 156 with each other, and where none of the lower level passageways connect the vent grove 122 with the vent 119.

Figure 18:
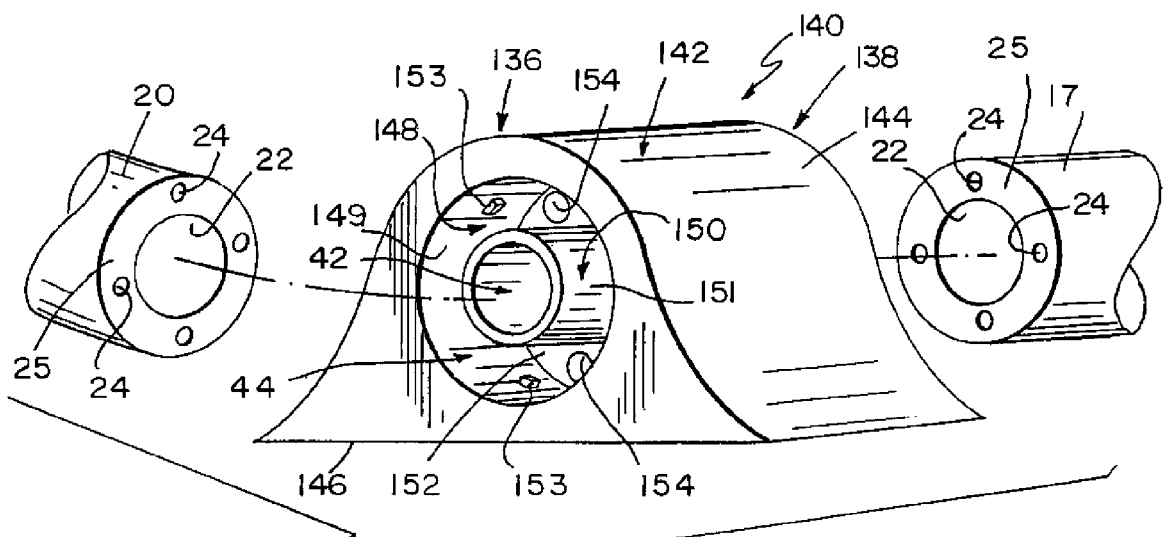
Figure 19:
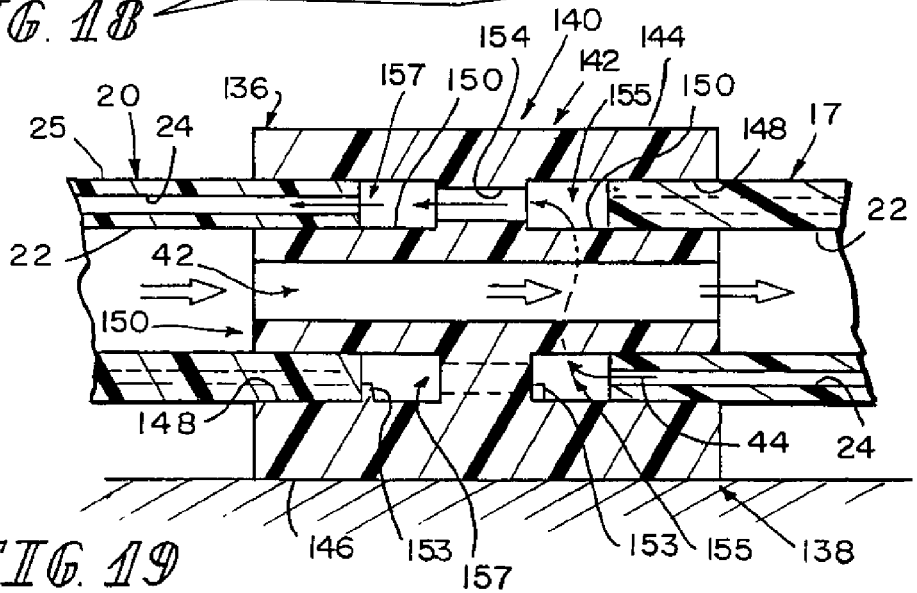

Referring now to FIGS. 17-19, a tube coupler 140 is provided for use with system 10. As shown in FIG. 17, coupler 140 is positioned between bandage 14 and assembly 180. It is within the scope of this disclosure, however, to position a tube coupler between bandage 14 and assembly 80 shown in FIG. 1. Coupler 140 connects or couples two multi-lumen tubes together. Coupler 140 allows a caregiver to disconnect a portion of system 10 between bandage 14 and assemblies 80 or 180. As shown in FIGS. 17-19, coupler 140 couples multi-lumen tube 20 to another multi-lumen tube 17.

Coupler 140 includes an outer body 142 having a curved upper surface 144 and a generally flat bottom surface 146. Outer body 142 defines a passageway 148 therethrough for receiving a portion of a multi-lumen tube at a first end 136 and at a second end 138. Passageway 148 is defined by an inner surface 149 of body 142. Coupler 140 further includes an inner conduit 150 which defines a portion of vacuum/irrigation passageway 42. Inner conduit 150 is positioned within passageway 148. A portion of vent passageway 44 is annular and is defined between inner surface 149 of body 142 and an outer surface 151 of inner conduit 150. Coupler 140 further includes a central partition 152 formed around conduit 150 and connected to inner surface 149. Partition 152 includes three generally evenly spaced holes 154 for the vented air to flow through.

An end of tube 20 is inserted into first end 136 of coupler 140 and an end of tube 17 is inserted into second end 138 of coupler 140, as shown in FIG. 19, so that inner conduit 150 is received within the inner lumen 22 of each tube 20, 17. As mentioned above, multi-lumen tubes 20, 17 include four outer lumens 24 formed in wall 25. As shown in FIG. 19, tubes 20, 17 are inserted into coupler 140 and are generally spaced-apart from partition 152 so that air flowing through the four outer lumens 24 of tube 17 flows into an open space 155 on the right side of partition 152, as shown in FIG. 19, through holes 154 of partition 152 and into an open space 157 located on the left side of partition 152 into outer lumens 24 of tube 20.

Tube coupler 140 may also be used to aide in effectively securing sealing film 13 of bandage 14 over or around tube 20. For example, coupler 140 may be placed on the patient's healthy skin adjacent the wound. The film 13 may then be placed over curved upper surface 144 of coupler 140 and effect a seal around coupler 140 to create a sealed environment between film 13 and the wound. Coupler 140, therefore, may also act to prevent leaks in the vacuum space created below film 13. Coupler 140 further includes a ridge or stop 153 coupled to inner surface 149 to each of the right and left sides of partition 152 to prevent each respective tube 20, 17 from abutting partition 152 and closing off vent lumens 24 from communication with the surrounding atmosphere. Each open space 155, 157, therefore, is defined between a respective stop 153 and partition 152, as shown in FIG. 19.

Figure 20:
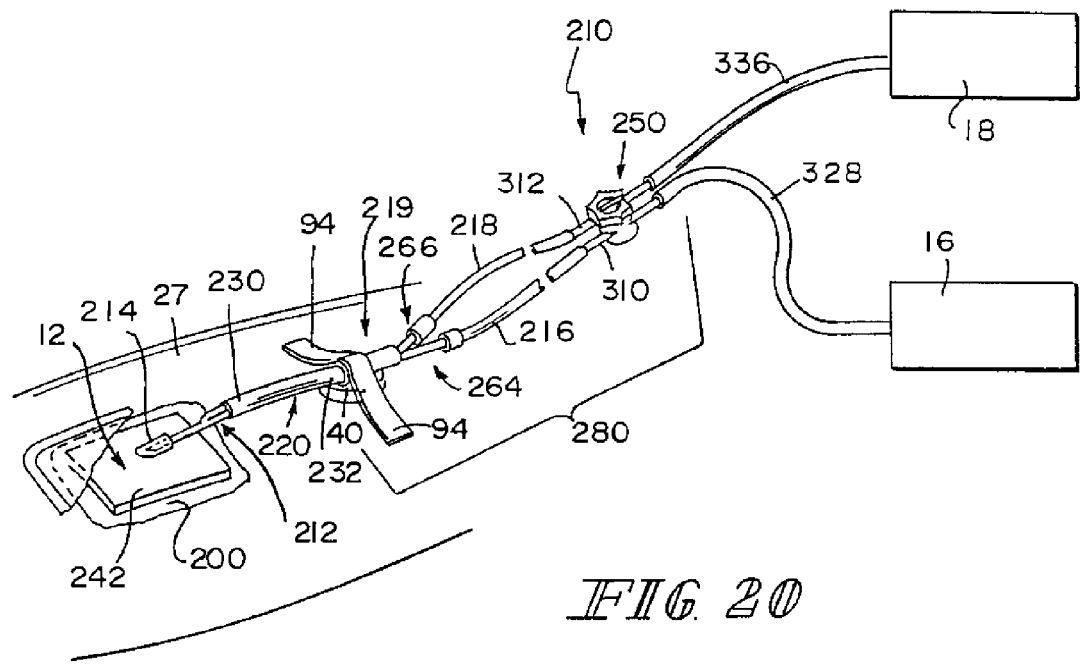
FIGS. 20-28 illustrate components of yet another wound care bandage system in accordance with the present disclosure for providing suction, irrigation, and ventilation to the wound.

Referring now to FIGS. 20-28, another illustrative wound care bandage system 210 is provided. System 210 operates similarly to system 10 described above and includes a vent-valve apparatus 280 to provide ventilation while allowing a user to toggle between a vacuum therapy mode and an irrigation therapy mode. As shown in FIG. 20, bandage 14 is coupled to a vent 219 via an alternative multi-lumen tube 220. Specifically, member 12 of bandage 14 is coupled to a "Y-connector" 212 of the system 210 which is coupled to tube 220. Y-connector 212 is shown in more detail in FIGS. 22 and 24 and is discussed in more detail below.

Vent-valve apparatus 280 includes a stopcock or switch valve 250 coupled to vent 219 via two single-lumen tubes 216, 218. Switch valve 250 is coupled to both vacuum source 16 and irrigation source 18 to provide selective communication between either the bandage 14 and vacuum source 16 or between bandage 14 and irrigation source 18, as described below.

Vent 219, similar to vent 19, is spaced apart from bandage 14 and is illustratively shown to be coupled to patient's healthy skin 27 by tape 94, for example. Vent 219 is able to provide ventilation to wound 200 (shown in FIG. 20) during the application of negative pressure to wound 200 and during irrigation of wound 200 because vent 219, similar to vents 19 and 119 are in communication with the surrounding atmosphere and with the wound 200.

The wound care bandage system 210 shown in FIGS. 20-28 incorporates three separate fluid paths. One fluid path is used exclusively for the purpose of venting the wound 200 with air from the surrounding atmosphere. A second fluid path is used to create a negative pressure adjacent the wound 200, while the third fluid path is used to irrigate the wound 200. Switch valve 250 acts to selectively communicate either the vacuum path or the irrigation path with the wound 200. The three fluid paths for ventilation, vacuum, and irrigation of wound 200 are provided by multi-lumen tube 220.

Figure 21:
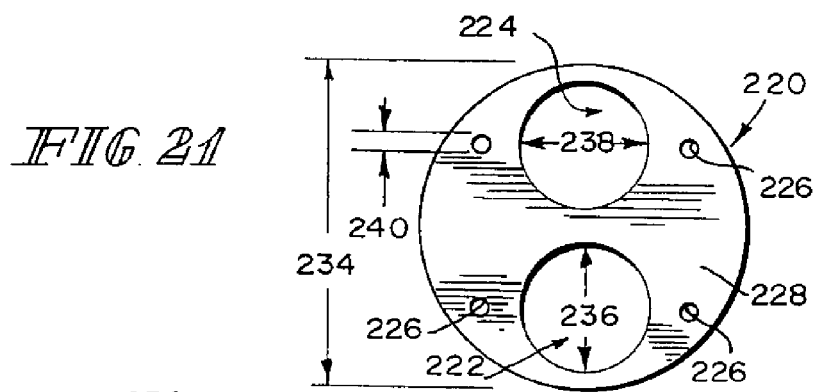
Figure 24:
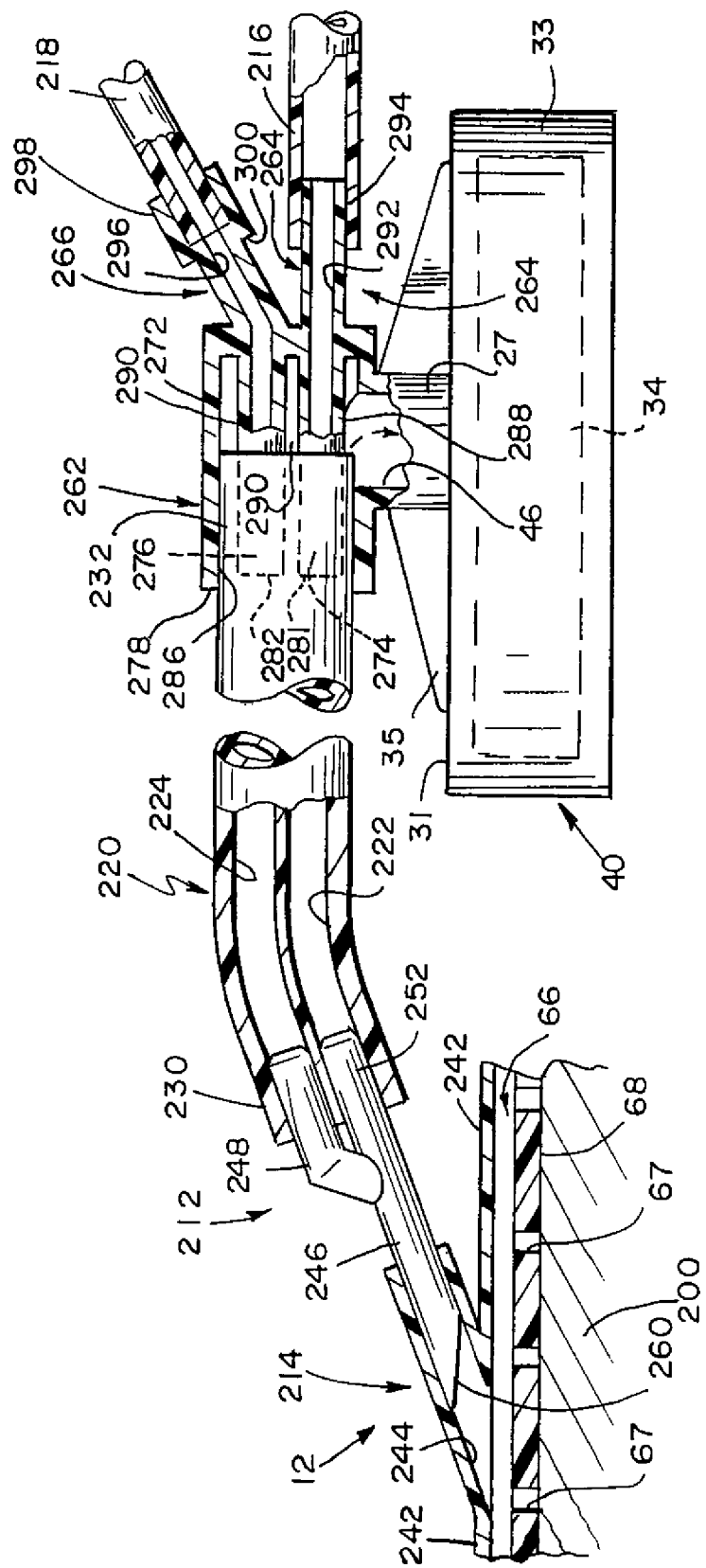

Multi-lumen tube 220 includes a vacuum lumen 222, an irrigation lumen 224, and four outer venting lumens 226 formed within and defined by a body 228, as shown in FIG. 21. Vacuum lumen 222 is in communication with vacuum source 16, irrigation lumen 224 is in communication with irrigation source 18, and each venting lumen 226 is in communication with the atmosphere through vent 219, as is described below. As shown in FIGS. 20 and 24, multi-lumen tube 220 is coupled to an alternative connector 214 of member 12 by Y-connecter 212, and is therefore in communication with the wound 200 at one end 230 and is coupled to vent 260 at another end 232.

Although tube 200 is shown to include four venting lumens 214, it is within the scope of this disclosure to include a multi-lumen tube having one or more venting lumens in communication with the surrounding atmosphere, one or more vacuum lumens in communication with the vacuum source 16, and one or more irrigation lumens in communication with the irrigation source 18. Illustratively, an outer diameter 234 of tube 220 is 0.375 inch (9.53 mm), a diameter 236 of vacuum lumen 222 is 0.125 inch (3.175 mm), a diameter 238 of irrigation lumen 224 is 0.125 inch (3.175 mm), and a diameter 240 of each outer venting lumen 226 is 0.020 inch (0.508 mm). Although tube 220 includes the above dimensions, it is within the scope of this disclosure to provide any suitable multi-lumen tube having lumens of any suitable size.

As mentioned above, Y-connecter 212 is provided for coupling with alternative connector 214 of vacuum bandage 14. Connector 214 is similar to connector 15 and is in communication with wound 200 through channels 66 and holes 67 of member 12. Connector 214 is different from connector 15 in that connector 214 is positioned at an angle relative to a top surface 242 of member 12 and includes a single angled passageway 244 (as shown in FIG. 24) rather than a vertical passageway connected to a horizontal passageway of connector 15 (as shown in FIG. 3). In the illustrative embodiment, the included angle between an axis along passageway 244 and the top surface 242 of member 12, when member 12 is in a flat configuration, is about 30 degrees.

Figure 22:
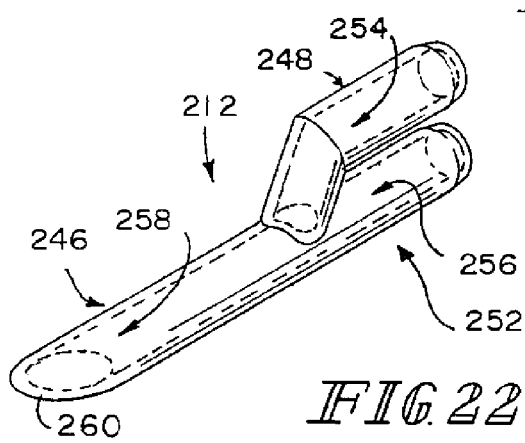

Illustratively, Y-connecter 212 includes a bandage portion 246, an irrigation portion 248, and a vacuum portion 252, as shown in FIG. 22. Irrigation portion 248 includes a passageway 254 forming a section of the irrigation passageway, vacuum portion 252 includes a passageway 256 forming a section of the vacuum passageway, and bandage portion 246 includes a passageway 258 forming a section of the vacuum/irrigation passageway. The passageway 254 of irrigation portion 248 and the passageway 256 of vacuum portion 252 each merge into passageway 258 of the bandage portion 246. Once bandage portion 246 of Y-connecter 212 splits into the irrigation portion 248 and the vacuum portion 252, the irrigation and vacuum passageways remain separate and distinct passageways through multi-lumen tube 220, vent 219, and switch valve 250 to the respective irrigation source 18 and vacuum source 16.

Bandage portion 246 is press fit into connector 214, as shown in FIG. 24, and includes an angled end 260 to lie adjacent to the top surface 242 of member 12. Irrigation portion 248 is similarly press fit into irrigation lumen 224 of tube 220 and vacuum portion 252 is press fit into vacuum lumen 222 of tube 220. In some embodiments, adhesive or sealant is applied to either or all of portions 246, 248, 252 to further enhance the connection between bandage portion 246 and connector 214 between irrigation portion 248 and tube 220, and between vacuum portion 252 and tube 220. Y-connecter 212 is provided to connect bandage 14 with multi-lumen tube 220 and vent 219.

Figure 23:
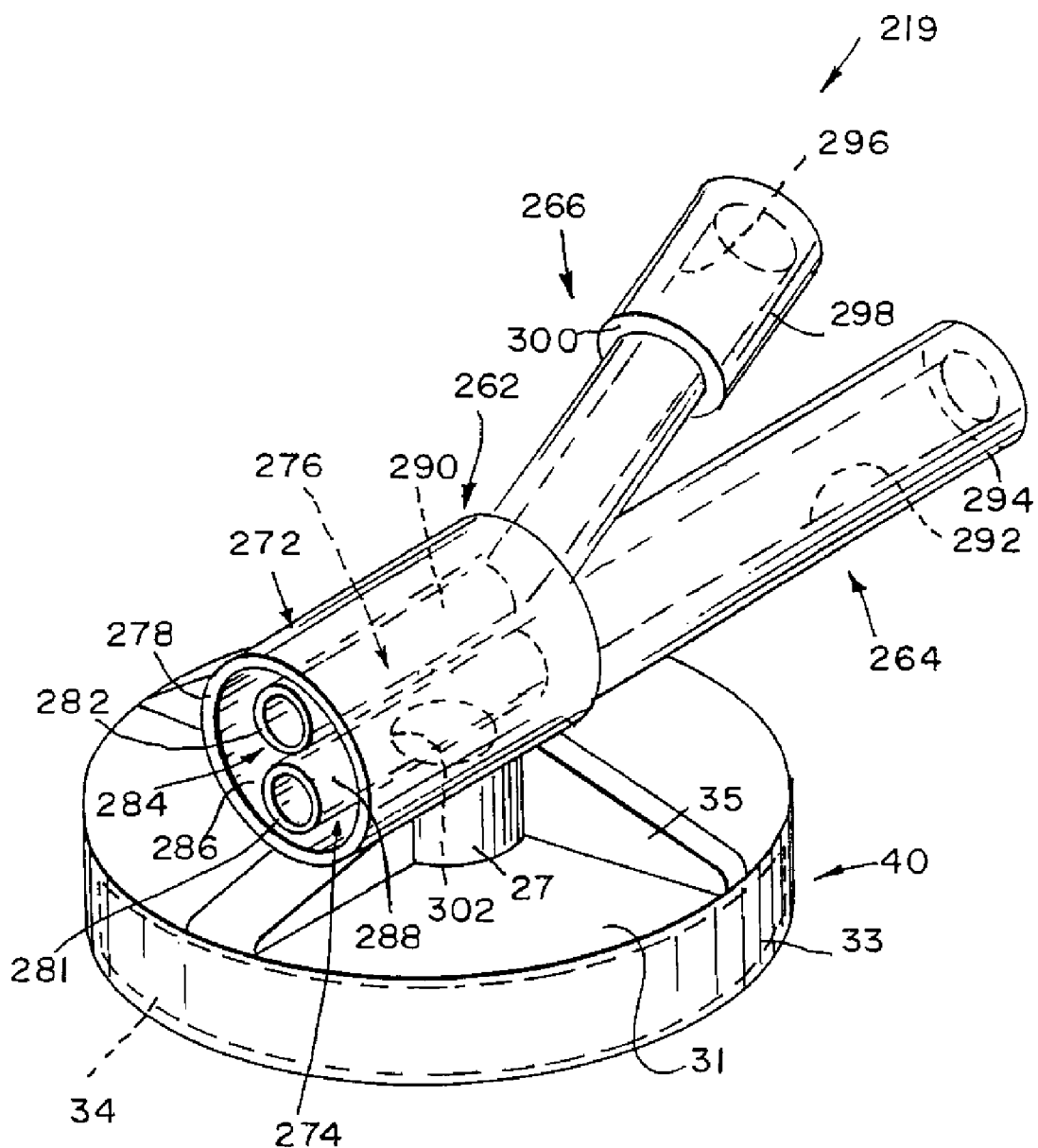

Referring now to FIG. 23, vent 219 includes a multi-lumen connector 262 for coupling with multi-lumen tube 220, a single-lumen vacuum connector 264 for coupling with a single-lumen tube, such as tube 216, and a single-lumen irrigation connector 266 for coupling with a single-lumen tube, such as tube 218 (as shown in FIG. 20). Tubes 216 and 218 are also coupled to switch valve 250 as shown in FIG. 20 and described in more detail below. It is also within the scope of this disclosure to eliminate the use of tubes 216 and 218 so that vent 219 is coupled directly to switch valve 250. Similar to vents 19, 119, vent 219 further includes filter 34 (shown in phantom), housed within filter housing 40, in communication with multi-lumen connector 262.

Multi-lumen connector 262 includes an outer conduit 272, an inner vacuum conduit 274, and an inner irrigation conduit 276, as shown in FIG. 23. Both vacuum conduit 274 and irrigation conduit 276 are located within outer conduit 272. An edge 278 of outer conduit 272 is substantially coplanar with an edge 281 of vacuum conduit 274 and an edge 282 of irrigation conduit 276. Vacuum conduit 274 is in communication with vacuum source 16 through switch valve 250 and defines a portion of the vacuum passageway. Irrigation conduit 276 is in communication with the irrigation source 18 through switch valve 250 and defines a portion of the irrigation passageway. Outer conduit 252 is in communication with the surrounding atmosphere and defines a portion of the vent passageway.

As shown in FIG. 24, vacuum conduit 274 is received within vacuum lumen 222 of tube 220. Body 228 of tube 220, which includes outer venting lumens 226, is received within a space 284 defined between a cylindrical inner surface 286 of outer conduit 272 and cylindrical outer surfaces 288, 290 of vacuum and irrigation conduits 274, 276, respectively (as shown in FIG. 23). Tube 220 is press fit into the space 284 so that the outer surface of tube 220 abuts cylindrical inner surface 286 of outer conduit 272, so that an inner surface of vacuum lumen 220 abuts the cylindrical outer surface 288 of the vacuum conduit 274, and so that the inner surface of irrigation lumen 224 abuts the cylindrical outer surface 290 of the irrigation conduit 276. In some embodiments, an adhesive material or sealant is applied to the appropriate surfaces of tube 220 and multi-lumen connector 262 to enhance the connection between tube 220 and vent 219.

As shown in FIG. 23, a ridge or stop (not shown) is coupled to and positioned between outer surface 288 of vacuum conduit 274 and outer surface 290 of irrigation conduit 276 to prevent tube 220 from being inserted too far within connector 262 and thus sealing off outer lumens 226. The stop prevents vent passageway from becoming closed off and keeps vent passageway open to receive air from the surrounding atmosphere. Illustratively, vent 219 includes one stop, however, it is within the scope of this disclosure to include a vent having any number of stops or the like to prevent the vent passageway from becoming closed off from the surrounding atmosphere.

Vacuum connector 264 of vent 219 includes an inner surface 292 defining a portion of the vacuum passageway and an outer surface 294. Vacuum connector 264 is in communication with vacuum conduit 274 of multi-lumen connector 262, as shown in phantom in FIGS. 23 and 24. Illustratively, single-lumen tube 216, coupled to vacuum source 16, is press fit into vacuum connector 264, as shown in FIG. 24. Tube 216 may further be permanently or temporarily bonded to vacuum connecter 264 through the use of an adhesive material applied to the appropriate surfaces of tube 216 and connecter 264.

Irrigation connector 266 of vent 219 similarly includes an inner surface 296 defining a portion of the irrigation passageway and an outer surface 298 including a shoulder 300. Irrigation connector 266 is in communication with irrigation conduit 276 of multi-lumen connector 262, also shown in FIGS. 23 and 24. Illustratively, single-lumen tube 218 is press-fit into irrigation connector 266, as shown in FIG. 24. Tube 218 may further be permanently or temporarily bonded to irrigation connector 266 through the use of an adhesive material applied to the appropriate surfaces of tube 218 and connector 266. It is within the scope of this disclosure, however, to connect tubes 216 and 218 to the respective irrigation and vacuum connectors 266, 264 through the use of a barb or a luer lock connection, for example.

Outer conduit 272 of multi-lumen connector 262 further includes an opening or aperture 302 in communication with the surrounding atmosphere. Housing 40 for filter 34 is coupled to multi-lumen connector 262 so that a passageway 46 of housing 40 connects space 284 with the filter 34 and the surrounding atmosphere. Passageway 46 extends radially away from outer conduit 272 and is generally perpendicular to an axis running through vacuum conduit 274. Passageway 46 is defined by cylindrical wall 27.

In operation, vent 219 is used during both vacuum and irrigation modes of the system. As mentioned before with respect to vents 19 and 119, vent 219 provides increased air flow through bandage 14 and above wound 200. Vent 219 also creates an open system and prevents the system from becoming static. Vent 219 further maintains separate vacuum and irrigation passageways. As mentioned before with respect to vents 19, 119, it is within the scope of the disclosure for the caregiver to close off vent 160 while vacuuming or irrigating wound 200. Vent 219 may also be closed in a number of ways. For example, a cap or a valve (not shown) may be coupled to filter 34 or filter housing 40 to prevent air flow through filter 34. It is within the scope of this disclosure to include a vent having other suitable means of preventing air flow therethrough.

Referring now to FIGS. 25-28, the stopcock 250 of system 210 includes a diverter or handle 314 and a body 316 defining an aperture 318 for receiving at least a portion of the handle 314. Handle 314 includes a grip 320 and a hub or stem 322 coupled to the grip 320. Hub 322 is received within aperture 318 of body 316. Stopcock or switch valve 250 further includes a vacuum conduit 310 having a first portion 324 coupled to tube 216 and a second portion 326 coupled to a single-lumen tube 328, as shown in FIG. 20. Tube 328, is coupled to vacuum source 16, as shown in FIG. 20. As shown in FIGS. 25-28, vacuum conduit 310 defines a portion of the vacuum passageway through body 316. Each single-lumen tube 216, 328 is coupled to the respective first portion 324 and second portion 326 of the stopcock 250 through the use of luer locks (not shown). It is within the scope of this disclosure, however, to connect tubes 216, 328 to stopcock 250 in another suitable manner such as through the use of a barb, by press-fitting each tube 216, 328 onto conduit 310 of stopcock 250, or by slip-fitting each tube 216, 328 into conduit 310, and including the use of adhesive material to permanently or temporarily bond each tube 216, 328 to conduit 310.

Figure 25:
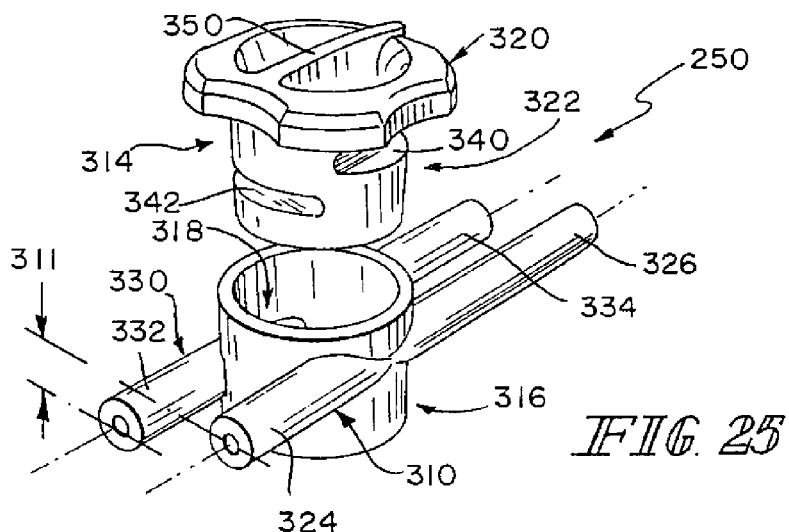

Stopcock 250 further includes an irrigation conduit 330 having a first portion 332 coupled to tube 218 and a second portion 334 coupled to a single-lumen tube 336. Tube 336 is coupled to irrigation source 18, as shown in FIG. 20. Irrigation conduit 330 defines a portion of the irrigation passageway through body 316 of stopcock 250. As shown in FIG. 25, irrigation conduit 330 lies below vacuum conduit 310 as indicated by a distance 311 so that the irrigation conduit 330 and vacuum conduit 310 are positioned to lie in separate horizontal planes. Tubes 218, 336 may be coupled to irrigation conduit 330 by the same or similar means as those discussed above with respect to tubes 216, 328 and vacuum conduit 310.

Hub 322 of handle 314 includes a first or vacuum cut-out portion 340 and a second or irrigation cut-out portion 342. Similar to conduits 310 and 330, cut-out portions 340, 342 do not lie in the same horizontal plane. When hub 322 is received within aperture 318 of body 316, vacuum cut-out portion 340 lies in the same horizontal plane as vacuum conduit 310 and irrigation cut-out portion 342 lies in the same horizontal plane as irrigation conduit 330.

Figures 26, 27, 28:
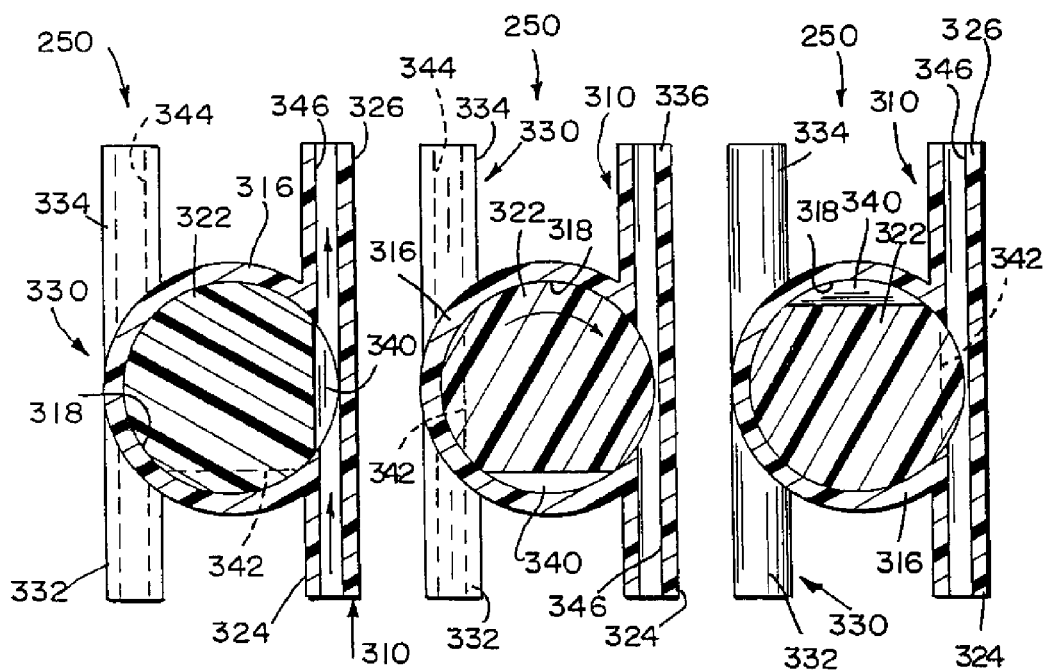

Handle 314, and thus hub 322, is rotatable relative to body 316. Handle 314 is able to be positioned by a caregiver to align the vacuum cut-out portion 340 with the vacuum conduit 310, as shown in FIG. 26, or to align the irrigation cut-out portion 342 with the irrigation conduit 330, as shown in FIG. 27. Further, handle 314 may be rotated to an "off" position where neither cut-out portion 340, 342 is aligned with either of the conduits 310, 330, as shown in FIG. 28. Thus, passageways 344, 346 through conduits 310, 330 each communicate with aperture 318 of body 316.

Referring to FIG. 26, the stopcock 250 is in a vacuum position where vacuum cut-out portion 340 is aligned with vacuum conduit 310, as mentioned above. Vacuum cut-out portion 340 connects first portion 324 of vacuum conduit 310 with second 326 of vacuum conduit 310 so that vacuum source 16 is able to create a negative pressure adjacent the wound 200. When stopcock 250 is in the vacuum position, irrigation cut-out portion 342 is not in communication with the irrigation conduit 330.

Rotating handle 314 about 90 degrees clockwise from the vacuum position aligns irrigation cut-out portion 342 with irrigation conduit 330 in an irrigation position shown in phantom in FIG. 27. Irrigation cut-out portion 342 connects first end 332 of irrigation conduit 330 with second end 334 of irrigation conduit 330 so that the irrigation source 18 is able to send fluids through stopcock 250 to wound 200. When stopcock 250 is in the irrigation position, vacuum cut-out portion 340 is not in communication with the vacuum conduit 310.

To move the stopcock 250 to the "off" position (shown in FIG. 28), the caregiver may either rotate the handle 180 degrees in either direction from the irrigation position (shown in FIG. 27) or the caregiver may rotate the handle 90 degrees in the counter-clockwise direction from the vacuum position (shown in FIG. 26). As mentioned above, neither cut-out portion 340, 342 communicates with either conduit 310, 330 when stopcock 250 is in the "off" position.

As shown in FIG. 25, grip 320 of handle 314 includes an indicator 350 to indicate to the caregiver whether the stopcock 250 is in the vacuum position, irrigation position, or off position. It is within the scope of this disclosure to include a seal, gasket, or o-ring (not shown) between hub 322 and body 316 of stopcock 250 to create a seal between the two components.

Figure 29:
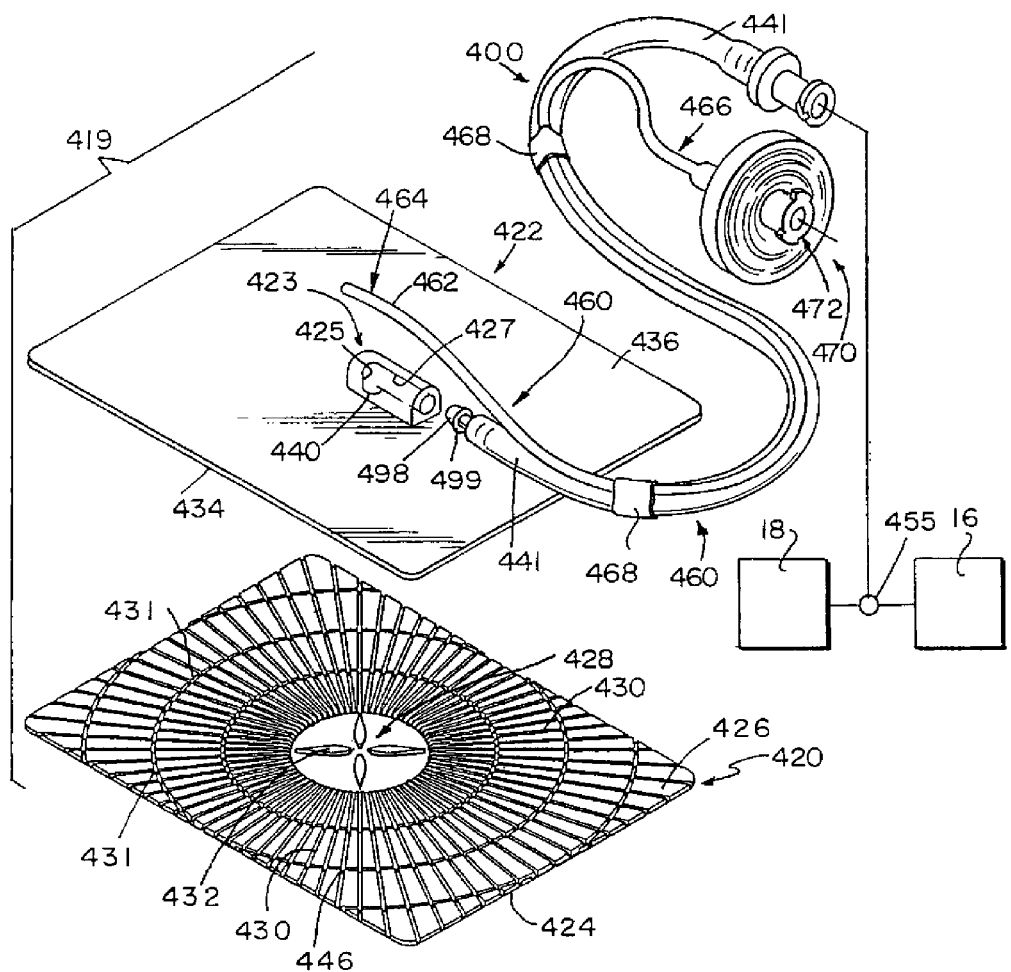
FIGS. 29-31 illustrate components of still another vacuum bandage system of the present disclosure which provides suction, irrigation, and ventilation to a wound.
Figure 30:
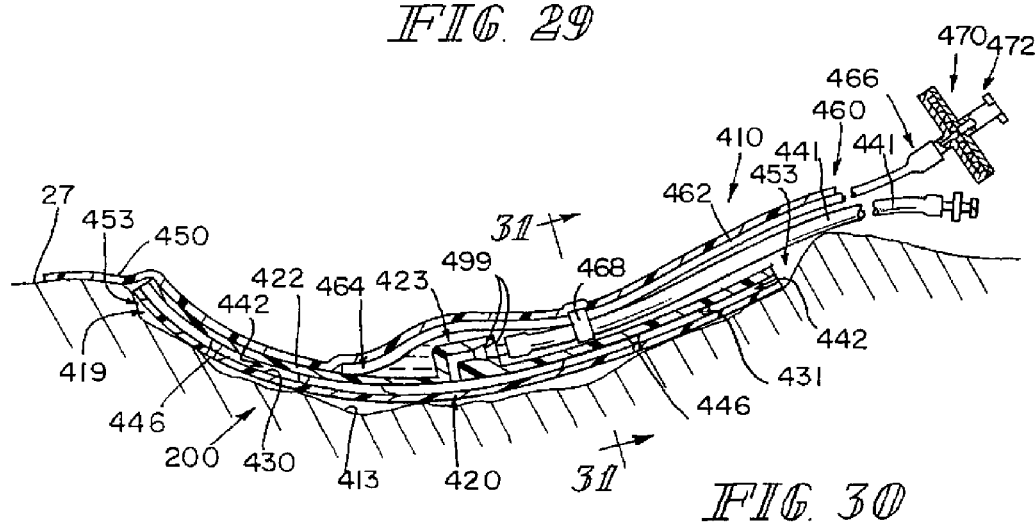

Looking now to FIGS. 29 and 30, yet another wound care bandage system 400 is provided which has the capability to create negative pressure adjacent wound 200, to irrigate wound 200, and to ventilate wound 200. Ventilated vacuum bandage system 400 is provided for use with wound 200 having a wound surface 413. The system 400 includes a wound dressing member 419 similar to wound dressing member 12, shown in FIG. 24, a vacuum source 16, an irrigation source 18, and a vent 460 in communication with the member 419. The vent 460 is also in communication with the surrounding atmosphere to provide increased air flow above the wound surface 413 and through the member 419 particularly when the vacuum source 16 is operating to create a negative pressure above the wound 200. As is herein defined with respect to all embodiments disclosed herein, the term "vent" is or includes any passageway to the atmosphere, unless noted otherwise.

In one illustrative embodiment, a vacuum bandage 410 is provided for use with wound 200 having wound surface 413, shown in FIG. 30. Bandage 410 includes the wound dressing member 419 and a vent 460 in communication with member 419 as shown in FIGS. 29 and 30. Member 419 is illustratively thin and flexible and includes a wound contacting layer 420 and a cover 422 coupled to the layer 420. Member 419 also includes a connector 423 coupled to cover 422 for communication with vacuum source 16 and/or irrigation source 18.

Vacuum bandage 410 is coupled to vacuum source 16 and irrigation source 18 through the use of a switch valve 455, as shown diagrammatically in FIG. 29. Switch valve 455 may be the same as or similar to stopcock 50 and/or assemblies 80, 180, described above, for example. Similar to bandage 14, bandage 410 also promotes the healing of large wound 200 by providing vacuum therapy to the wound 200 to promote blood flow and remove exudate from wound surface 413 and by providing for irrigation of the wound 200 with fluids such as saline, for example.

Vent 460 of system 400 is provided for increased air flow through bandage 410 and above wound 200 while vacuum source 16 applies suction to wound 200. Without vent 460, a generally closed system is created between vacuum bandage 10 and vacuum source 14. Vent 460, similar to vents 19, 119, 219 discussed above, acts to prevent the system 400 from becoming static by drawing air in from the surrounding atmosphere around bandage 410. Air is drawn through vent 460 to bandage 410 to create airflow above wound 200, through member 419, and out through a vacuum tube 441 coupled to vacuum source 16. A wound care technique disclosing ventilation of the wound is provided in the article "No wound is too big for resourceful nurses" by Margaret Wooding-Scott, RN, CCRN, Barbara Ann Montgomery, RN, ET, and Deborah Coleman, RN, MS, CS as published in the December 1988 edition of the magazine RN.

Referring now to member 419, layer 420, cover 422, and connecter 423 are each made of a medical grade silicone or other type of pliable elastomer. Two companies, for example, which manufacture such medical grade silicone are GE Silicones and NuSil Technology. It is within the scope of this disclosure, however, to include a member made of any suitable type of material. Illustratively, member 419 is made of material that is non-porous and non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of member 419. However, as mentioned above, it is within the scope of this disclosure to include a bandage having a member made of any suitable material to communicate the negative pressure from the vacuum source to the wound. Further, layer 420, cover 422, and connecter 423 may each be molded to include anti-microbial constituents. For example, it is within the scope of this disclosure to impregnate member 419 with silver ions which are known anti-microbials.

Illustratively, member 419, including layer 420, cover 422, and connecter 423, is also made of a generally non-adhesive material. Therefore, wound contacting layer 420, which lies generally adjacent to the wound surface 413, does not adhere to the wound surface 413. Further, member 419 is illustratively solid in nature and generally non-compressible. Member 419 is also illustratively transparent. Therefore, a caregiver or user is able to see the wound 200 through member 419 when member 419 is placed adjacent to wound surface 413. This transparency allows the caregiver to view the progress of the healing of the wound 200.

Layer 420 includes a wound facing surface 424 and an upper or opposite surface 426. Wound facing surface 424, or portions thereof, contact and conform to the wound surface 413. Opposite surface 426 includes a central area 428 and a plurality of channels 430 spaced-apart from and extending radially away from central area 428. Central area 428 is recessed relative to the portions of upper surface 426 between channels 430. As shown in FIG. 29, channels 430 are open at the sides and ends of member 419. Opposite surface 426 further includes concentric channels 431. Illustratively, each channel 430, 431 is 0.030 inch (0.762 mm) wide and 0.030 inch (0.762 mm) deep. It is within the scope of this disclosure, however, to include channels 430, 431 of opposite surface 426 having other suitable widths and depths suitable for the present application. Central area 428 of layer 420 is provided to communicate with the vacuum source 16 and irrigation source 18 through a port 440 of cover 422, as will be described below.

Illustratively, a plurality of radially extending protrusions or bosses 432 are positioned around central area 428. Bosses 432 are positioned between central area 428 and channels 430, 431, as shown in FIG. 29. Bosses 432 are provided to prevent central area 428 from collapsing in on port 440 of cover 422 to form a seal and effectively block air flow through port 440 while suction is applied to the bandage 410. Port 440 communicates with the vacuum source 16 and/or the irrigation source 18 via connecter 423 and tube 441, as shown in FIGS. 29 and 30. Tube 441 is coupled to connecter 423 by a barbed tube coupler 498, similar to tube coupler 11 described above. Tube 441 may also be coupled directly to connecter 423.

As mentioned above, port 440 is in communication with central area 428 of layer 420. Illustratively, four bosses 432 are shown in FIG. 29. However, it is within the scope of this disclosure to provide any number of bosses 423 or the like around central area 428 of layer 420 to prevent central area 428 from sealing off port 440 of cover 422 as suction is applied to bandage 410. Further, it is within the scope of this disclosure to include a boss or bosses having any shape in order to prevent central area 428 from sealing off port 440 when vacuum source 16 is running.

Connecter 423, as shown in FIGS. 29 and 30 is a tubal port coupled to a top surface 436 of cover 422 and in communication with port 440 of cover 422. As mentioned before, it is within the scope of this disclosure for connecter 423 to be a separate component of member 419 which is coupled to cover 422 or for connecter 423 to be coupled to cover 422 by being molded integrally with cover 422. Connecter 423 includes a passageway formed at a right-angle. Thus, the passageway in connecter 423 has a vertical portion 425 that communicates with port 440 and a horizontal portion 427 that communicates with vertical portion 425. Connecter 423 connects with tube 441 through the coupler 498 to provide a horizontal tube attachment for tube 441. Cover 422 includes a bottom surface 434 and top surface 436, as shown in FIG. 29. Bottom surface 434 engages opposite surface 426 of layer 420, as shown in FIG. 30.

In some embodiments, member 419 is formed by heat sealing opposite surface 426 of layer 420 and bottom surface 434 of cover 422 together and by heat sealing connecter 423 to top surface 436 of cover 422. For example, each of connecter 423, cover 422 (or the combination of cover 422 and connecter 423), and layer 420 may be pre-shaped and formed from semi-cured silicone. Once the connecter 423, cover 422, and layer 420 are placed together appropriately, the entire member 419 may be heated to heat seal and cure each of the three components to one another. Alternatively, for example, the cover 422 only may be made from semi-cured silicone while the connecter 423 and layer 420 may be made from fully cured silicone. Once placed together and heated, connecter 423 and layer 420 will heat seal to cover 422. Semi-cured silicone may be bought and pre-molded from a manufacturer such as NuSil Technology, for example.

Although the method of heat sealing the cover 422, connecter, and layer 420 to each other is disclosed, it is within the scope of this disclosure to form member 419 by coupling layer 420, cover 422, and connector 423 together by any other suitable means such as through the use of adhesives, for example. Further, it is within the scope of this disclosure to provide a member 419 where cover 422 lies adjacent to, but is not coupled to, layer 420.

As mentioned above, cover 422 is coupled to layer 420 and connecter 423 is coupled to cover 422 to form member 419. Cover 422 and layer 420 cooperate to form distinct passageways 442 of member 419 defined by channels 430, 431 of layer 420 and lower surface 434 of cover 422. Passageways 442 extend from the outer edges of member 419 and are in communication with central area 428 of layer 420. Central area 428 of layer 420 is in communication with port 440 of cover 422 which is in communication with the vacuum and/or irrigation sources 16, 18, via connecter 423, and tube 441. Therefore, passageways 442 are in communication with the vacuum and/or irrigation sources 16, 18.

Layer 420 includes through holes 446 which extend from channels 430, 431 to wound facing surface 424, as shown in FIG. 30. Illustratively, holes 446 are distinct and are provided to communicate with channels 430, 431 of layer 420. Holes 446 therefore communicate with passageways 442 of member 419 and the vacuum and/or irrigation sources 16, 18 as well to allow the suction from the vacuum source 16 and/or the fluid from the irrigation source 18 to reach the wound bed surface 413 via the holes 446. Illustratively, holes 46 are 0.020 inch (0.508 mm) in diameter and are spaced approximately 0.500 inch (12.700 mm) apart along channels 430, 431 of layer 420. It is, however, within the scope of the disclosure to include holes having other suitable sized diameters and/or other suitable spacing that allow for the removal of exudate without clogging.

Bandage 410 further includes a sealing layer or film 450 that is placed over cover 422 and around tube 441, as shown in FIG. 30. Film 450 acts as an outer cover of the bandage 410 and covers the entire wound 412 by extending over wound 412 and attaching to the patient's healthy skin 452, also as shown in FIG. 30. Preferably, film 450 is an occlusive or semi-occlusive material which allows water vapor to permeate through. Because of this characteristic, the film 450 is referred to as Moisture Vapor Transmission Rate film or MVTR film. The products TEGADERM® brand sealing film made by 3M Corporation, and OPSITE FLEXIGRID® semi-permeable dressing made by Smith & Nephew can be used for film 450, for example. Film 450 is approximately 0.003 inch (0.076 mm) thick. However, it is within the scope of this disclosure to include any occlusive or semi-occlusive film 450 having another thickness. Film 450 is provided to create a sealed environment below the film 450 and around the wound 200 in which a vacuum or negative pressure can be maintained as provided by vacuum source 16. Film 450 therefore creates a vacuum space 453 below film 450 and above wound surface 413.

As shown in FIG. 30, sealing film 450 is positioned adjacent to top surface 436 of cover 422. It is within the scope of this disclosure, however, for bandage 410 to further include a packing material or filler such as gauze, for example, positioned between film 450 and member 419.

It is also within the scope of this disclosure to provide a bandage (not shown) having a self-sealing member which seals about the wound 412 to the patient's healthy skin 27 to provide a vacuum space between the member and the wound surface 413. In other words, it is within the scope of this disclosure to include a bandage having a sealing means without the use of sealing film 450. For example, it is within the scope of this disclosure to include a wound contacting layer of the member having an adhesive positioned about the outer perimeter of the wound contacting surface of the layer. The adhesive perimeter would be provided to seal to the patient's healthy skin 27 surrounding wound 200. The adhesive would, therefore, permit the member to be self-sealing such that a vacuum or negative pressure can be created and maintained above wound surface 413 without the use of sealing film 450. It is also within the scope of this disclosure to provide any member having an adhesive for attachment to the patient's healthy skin surrounding the wound so that the member is self-sealing and able to maintain a negative pressure above the wound without the use of a sealing film. For example, the wound contacting layer may be sized smaller than the cover and the bottom surface of the cover may include an outer adhesive perimeter for coupling with the patient's surrounding healthy skin.

As shown in FIG. 30, member 419 of bandage 410 has a smooth wound facing surface 424. Wound facing surface 424 may also be textured or roughened and/or may include ribs, protrusions, channels, or spacers, or a single rib, protrusion, channel or spacer design. By providing member 419 with one or more ribs, protrusions, channels, spacers, etc., a space is created between surface 424 of layer 420 and wound surface 413. Through holes 446 communicate with this space to permit vacuum source 16 to establish a generally uniformly distributed vacuum or negative pressure to the wound surface 413 to draw blood from the body to the wound surface 413 and to draw exudate from the wound 412 through holes 446, into channels 430, 431 and passageways 442, and out port 440 of cover 422.

Although bandage 410 is described above, it is within the scope of this disclosure for the ventilated vacuum bandage system to include any suitable bandage or wound dressing member coupled to the vacuum source 16 to communicate negative pressure from the vacuum source 16 to the wound 412. Bandage 410, therefore, is merely an illustrative bandage for use with the wound care bandage systems disclosed herein.

The vacuum or negative pressure which draws blood from the body to the wound surface 413 and draws exudate from the wound 200 up through member 419 promotes the healing of wound 200. As wound 200 heals, granulations form along the wound surface 413. Granulations, therefore, are the replacement within the wound bed of tissue lost. As the granulations fill in the wound bed causing the wound 200 to heal, member 419 rides up on the wound surface 413 on top of the granulations which are formed.

As mentioned above, port 440 of cover 422 communicates with vacuum source 16 and/or irrigation source 18 via connector 423 and tube 441. As shown in FIG. 29, switch valve 455 is provided which allows the caretaker to switch between the use of the vacuum source 16 and the irrigation source 18. It will be appreciated that a mechanism other than the switch valve 455 may be used to selectively couple the vacuum source 16 or the irrigation source 18 to the bandage 410. Simple tube clamps, for example, may be used selectively to open and close the tube set provided with bandage 410. When valve 455 is switched to operate the vacuum source 16, the vacuum suction draws exudate up through holes 446 and radially inwardly through passageways 442 toward port 440 and finally through connector 423 and tube 441. Although tube 441 has been referred to as vacuum tube 441, tube 441 may also be used as an irrigation tube carrying liquid to the wound 200 from irrigation source 18, as described above.

As mentioned above, bandage 410 includes vent 460 similar to vents 19, 119, 219 described above. Vent 460 also operates to increase air flow through the wound 200 and the passageways 442 of member 419 while vacuum source 16 applies suction to wound 200. Without vent 460 a generally closed system is created between vacuum bandage 410 and vacuum source 414. For example, in bandages without vent 460, once the requisite amount of air in the tubing 441 and below sealing film 450 within vacuum space 453 has been removed by the vacuum source 16 to create a predetermined negative pressure at wound surface 413, it is possible for the system to become generally static inhibiting much, if any, fluid flow from wound surface 413 through passageways 442 and out port 440 and connector 423. Vent 460, however, opens the system to aspirate the passageways 442 and tube 41 of the system which promotes removal of debris that may be clogging the system.

Vent 60 acts as a first port of bandage 410 and port 440 of member 419 acts as a second port of bandage 410. Bandage 410, therefore, includes a first port in communication with the surrounding atmosphere above or around bandage 410 and a second port in communication with the vacuum source 16. When vacuum source 16 is running, a pressure differential is initially created as vacuum source 16 draws more air out from beneath sealing film 450 than is drawn in from the surrounding atmosphere through vent 460. Therefore, a negative pressure is created above wound 200. Once a desired negative pressure above wound 200 is reached, that negative pressure may be maintained so that the amount of air flow into the bandage through vent 460 is generally equal to the amount of air flow out of the bandage 410 through connecter 423 and tube 441 by vacuum source 16. The two ports of bandage 410 allow an air flow current to be created beneath the film 450 to generally prevent the bandage 410 and vacuum source 16 system from becoming static.

Figure 31:
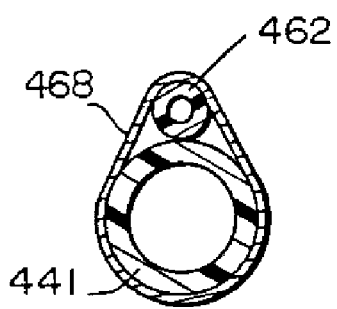

As shown in FIGS. 29 and 30, vent 460 comprises a vent line or tube 462 having a first end 464 and an opposite second end 466. Illustrative vent line 462 runs parallel to tube 441 and is coupled to tube 441 by one or more couplers 468, as shown in FIGS. 30 and 31. First end 464 is positioned to lie below sealing film 450 and above member 419. As shown in FIG. 30, first end 464 is adjacent top surface 436 of cover 422 and second end 466 of vent line 462 is positioned outside the vacuum space 453 defined between wound surface 413 and sealing film 450. Thus, second end 466 communicates with the surrounding atmosphere to draw air from the surrounding atmosphere into the system and through passageways 442 of member 419. Although vent 460 is illustrated as a tube, it is within the scope of this disclosure for vent 460 to include any type of conduit or passage which provides communication between the atmosphere surrounding the bandage 410 and the passageways 442 of the bandage 410.

An air filter 470 similar to filter 34, described above, is coupled to second end 466 of vent line 462 as shown in FIGS. 29 and 30. Illustratively, air filter 470 is a 0.2 micron antimicrobial filter for preventing bacteria and other microorganisms in the atmosphere from entering the wound space below film 450. Filter 470 is also hydrophobic. Such an air filter, for example, is made by W.L. Gore & Associates, Inc. of Elkton, Md. A cap or a valve 472 is also coupled to second end 466 of vent line 462. As shown in FIGS. 29 and 30, filter 470 is positioned between end 466 and valve 472. Valve 472 allows a user to manually control and adjust the amount of air flow into vent line 462. For example, valve 472 is movable between a fully closed position and a fully opened position. In the fully closed position, no air flow is permitted through valve 472 and the system operates as a closed system. In the fully open position, a maximum amount of air is drawn in through the valve 472 and vent line 462 so that the system operates as an open system to aspirate the passageways 442 of member 419 and create fluid flow throughout the system. The valve 472 is also adjustable to any desired partially open position between the fully closed position and the fully open position. Therefore, the amount of air flow through vent line 462 is adjustable by the caregiver.

While the valve 472 is open or partially open and air is being drawn in through vent line 462, vacuum source 16 will maintain a negative pressure under sealing film 450 while vacuum source 16 is operating. In other words, the vacuum bandage 410 and vacuum source 16 act to initially vent less air into the system than is vacuumed out of the system to create a negative pressure above the wound 200. Once created, the negative pressure above the wound 200 is maintained by vacuum source 16 when vent line 462 is open. For example, even though vent line 462 is open, vacuum source 16 is still able to create a negative pressure above wound 200 as a result of the pneumatic resistance provided by the vent 460. The vent line 462 and air filter 470 create pneumatic resistance to the entry of air from the surrounding atmosphere into the space 453 above the wound 200 when the valve 472 is open, thus enabling the net effect to be a negative pressure above the wound 200 created by the vacuum source 16. In preferred embodiments, vent 460 is open or partially open while the vacuum source 16 is operating. It is within the scope of the disclosure, however, to close the vent 460 while the vacuum source is running.

Figure 32:
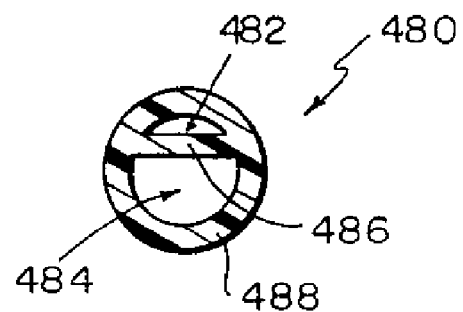
FIG. 32 is a sectional view of an alternative vent line and vacuum tube showing a multi-lumen tube having a vent passageway and a vacuum tube passageway formed therein and separated by a partition.
Figure 33:
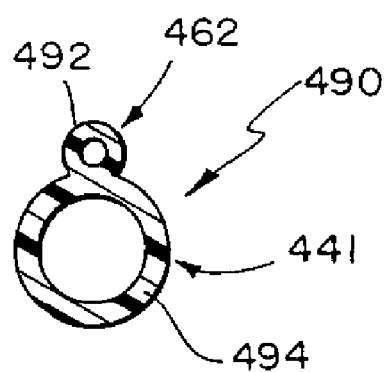
FIG. 33 is a sectional view of yet another vent line and vacuum tube combination showing an outer wall of the vent line and an outer wall of the vacuum tube integrally coupled to one another to form a single multi-lumen tube.

Although vent line 462 is shown to run parallel to tube 441, it is within the scope of this disclosure to position vent line 462 anywhere so long as first end 464 is positioned below sealing film 450 and second end 466 communicates with the surrounding atmosphere. Vent line 462 of the embodiment of FIGS. 29-31 comprises a separate tube formed independently from tube 441 and coupled to tube 441 by couplers 468, such as medical tape wrapped around tube 441 and vent line 462. FIGS. 32-33, as well as FIG. 4, described above, illustrate the cross sections of various alternative vent lines and vacuum/irrigation tube combinations.

The embodiments shown in FIGS. 32 and 33 as well as FIG. 4 illustrate parallel vent lines and vacuum/irrigation tubes which do not require a coupler 68, for example, to maintain their parallel relationship. A vent line and vacuum tube combination 480 is shown in FIG. 32. Combination 480 includes vent line passageway 482 and vacuum/irrigation passageway 484 separated from vent line passageway 482 by a partition 486. As shown in FIG. 32, combination 480 has a circular cross-section defined by an outer wall 488. Combination 480 is extruded or manufactured as a single tube having two passages or lumens, whereas vent line 462 and tube 441 of FIG. 31 are extruded or manufactured separately.

Another illustrative vent line and vacuum/irrigation tube combination 490 is shown in FIG. 33. In combination 490, vent line 462 and tube 441 are integrally coupled to each other. As illustrated, vent line 462 includes an outer wall 492 and tube 441 includes an outer wall 494. A portion of outer wall 492 is integrally coupled to a portion of outer wall 494. An external coupler 468, for example, is not required to maintain the parallel relationship of vent line 462 and tube 441 of combination 490. Further, combination 490 is extruded or manufactured as a single tube having two passages or lumens.

Yet another illustrative vent line and vacuum/irrigation tube combination is shown in FIG. 4 as multi-lumen tube 20 and was discussed above with reference to system 10. Multi-lumen tube is a single multi-lumen tube having outer wall 25 and a central, inner lumen or vacuum passageway 22. Passageway 22 may be coupled at one end to either the vacuum source 16 or the irrigation source 18 of system 410 and may be coupled at the other end to connecter 423 of member 419 via the barbed coupler 498, as shown in FIG. 3, and described in more detail below. As mentioned above with respect to system 10, multi-lumen tube 20 further includes four outer lumens or air vent passageways 24. Passageways 24 are formed within outer wall 25 and around central passageway 22. Passageways 24 are in communication with the atmosphere surrounding bandage 410 at one end and are in communication with the vacuum space 453 below sealing film 450. Combination 500 is also extruded or manufactured as a single tube.

As shown in FIGS. 29 and 30, barbed tube coupler 498 is received within tube 441 and horizontal passageway 427 of connector 423. Coupler 498 includes ridges 499 for preventing coupler 498 from separating from either tube 441 or connector 423. The vent line and vacuum tube combinations 480, 490 of FIGS. 32 and 33 as well as multi-lumen tube 20 of FIG. 4, are also coupled to connector 423 via coupler 498. For example, coupler 498 is received within tube passageway 484 of vent line and vacuum tube combination 480 leaving vent line passageway 482 free to draw air into the bandage 410 from the surrounding atmosphere. Coupler 498 is also received within tube 441 of combination 490 and vacuum passageway 22 of multi-lumen tube 20. It is within the scope of this disclosure to further include combinations 480, 490 where vent line passageway 482 and vent line 462 respectively, extend beyond tube passageway 484 and tube 441 to space first end 464 of vent line passageway 482 and vent line 462 away from tube passageway 484 and tube 441.

Vent 460, shown in FIGS. 29 and 30, comprises vent line 462, filter 470, and valve 472 as mentioned above. However, it is within the scope of this disclosure to provide any vent in communication with both vacuum space 453 and passageways 442 and with the surrounding atmosphere. In other words, a vent is provided for communication between an area outside bandage 410 and an area within bandage 410 below film 450 or any other sealing means to permit air to flow through the system to aspirate the passageways 442 of the system and to allow the system to operate as an open system. The vent 460 is provided to create a fluid flow path from outside the sealing means, through the sealing means to the member 419 and finally through the holes 446 and passageways 442 of the member 419 and out port 440 of member 419.

The air from vent 460 flows within the wound space 453 below film 450, or a similar sealing means, and above wound surface 413 of wound 200. For example, some air from the surrounding atmosphere reaches passageways 442 through openings at the peripheral edges of member 419 and some reaches passageways 442 through holes 446 via various gaps which may exist between wound surface 413 of wound 200 and wound facing surface 424 of member 419. Further, ribs, protrusions, nubs, or texturing on wound facing surface 424 act to promote air flow through holes 446 by providing a space between wound surface 413 and wound facing surface 424.

Although vent 460 is provided to create a fluid flow path from the surrounding atmosphere through the passageways 442 of member 419 and out port 440 of member 419, it is within the scope of this disclosure for vent line 462 of vent 460 to also be used as a separate irrigation line after filter 420 and valve 472 are detached from line 462. This second line may be connected to the irrigation source 18, for example, rather than be exposed to the surrounding atmosphere. It is therefore within the scope of this disclosure to connect second end 466 of vent line 462 to irrigation source 18 to permit irrigation of bandage 410 and wound surface 413 simultaneously with the operation of the vacuum source 16.

Although this invention has been described in detail with reference to certain embodiments, variations and modifications exist within the scope and spirit of the invention as described and defined in the following claims.

The invention claimed is:

1. A vacuum and irrigation wound bandage system for use with a wound having a wound surface, the system comprising:
   a vacuum source,
   an irrigation source,
   a connector coupled to the vacuum source and the irrigation source, the connector defining a first passageway and a second passageway,
   a bandage including (i) a wound dressing having a wound contacting surface adapted to be in contact with and generally conform to the wound surface and (ii) a cover positioned over the wound dressing and configured to seal to the patient's healthy skin surrounding the wound to create a vacuum space between the cover and the wound surface, and
   a multi-lumen tube having a first end in communication with the vacuum space and a second end coupled to the connector, the multi-lumen tube includes a central lumen in communication with the vacuum source such that fluid may move from the vacuum space to the vacuum source and at least four peripheral lumens each filled with air during operation of the vacuum and irrigation sources,
   wherein the central lumen couples with the connector such that the central lumen is in fluid communication with the first passageway, and the at least four peripheral lumens couple with the connector such that the at least four peripheral lumens are in fluid communication with each other through the connector and with the surrounding atmosphere through the second passageway.

2. The system of claim 1, wherein the cover is positioned over and seals around at least a portion of the multi-lumen tube.

3. The system of claim 1, further comprising a filter coupled to the connector for communication with the plurality of at least four peripheral lumens.

4. The vacuum bandage of claim 1, wherein the wound dressing includes a plurality of interconnected passageways formed therein and the central lumen is in communication with the passageways.

5. The system of claim 1, wherein the diameter of the central lumen is greater than the diameter of each of the peripheral lumens.

6. The system of claim 5, wherein the multi-lumen tube is generally circular in shape when viewed in cross-section.

7. The system of claim 1, further comprising a second connector in communication with the vacuum space, wherein the first end of the multi-lumen tube is coupled to the connector.

8. The system of claim 7, wherein the second connector includes a single lumen in communication with a central lumen of the multi-lumen tube.

9. A vacuum and irrigation wound bandage system for the treatment of a wound having a wound surface, the system comprising:
   a vacuum source,
   an irrigation source,
   a bandage having (i) a wound dressing including a wound contacting surface adapted to be in contact with and generally conform to the wound surface and (ii) a cover positioned over the wound dressing and configured to seal to the patient's healthy skin surrounding the wound to create a vacuum space between the cover and the wound surface,
   a first passageway between the vacuum source and the vacuum space,
   a second passageway between the irrigation source and the vacuum space,
   a multi-lumen tube including a first lumen and a second lumen, and
   a valve having a vent in communication with the surrounding atmosphere, the valve coupled to the multi-lumen tube and configured such that when the valve is in a first position the first lumen defines at least a portion of the first passageway and communication is substantially prevented through the valve between the second lumen and the vent, and when the valve is in a second position the first lumen defines at least a portion of the second passageway and communication is permitted through the valve between the second lumen and the vent.

10. The system of claim 9, wherein the valve is further configured such that when the valve is in a third position the first lumen defines at least a portion of the first passageway and communication is substantially permitted through the valve between the second lumen and the vent.

11. The system of claim 9, wherein the first lumen is a central lumen and the multi-lumen tube further includes a plurality of peripheral lumens each in communication with the vacuum space.

12. The system of claim 9, where the valve comprises a body and an inner barrel rotatably received in the body.

13. The system of claim 9, wherein the valve includes a vacuum connector coupled to the vacuum source, an irrigation connector coupled to the irrigation source, and a multi-lumen connector coupled to the multi-lumen tube.

14. The system of claim 9, further comprising a filter coupled to the vent.

15. A vacuum and irrigation bandage connectable to a vacuum source and an irrigation source and provided for use with a wound having a wound surface, the bandage comprising:

a wound dressing having a wound contacting surface adapted to be in contact with and generally conform to the wound surface, a cover positioned over the wound dressing and configured to seal to the patient's healthy skin surrounding the wound to create a vacuum space between the cover and the wound surface, a multi-lumen tube having (i) a first lumen configured for communication with both the vacuum space and the vacuum source, (ii) a second lumen configured for communication with both the vacuum space and the atmosphere surrounding the bandage, and (iii) a third lumen configured for communication with both the vacuum space and the irrigation source, a switch valve coupled to at least the first and third lumens of the multi-lumen tube and configured such that the switch valve is actuatable to (i) permit communication through the valve between the first lumen and the vacuum source while preventing communication through the valve between the third lumen and the irrigation source, and (ii) permit communication through the valve between the third lumen and the irrigation source while preventing communication through the valve between the first lumen and the vacuum source, and a filter coupled to the second lumen.

\* \* \* \* \*